(12) United States Patent  (10) Patent No.: US 6,599,272 B1
Hjertman et al.  (45) Date of Patent: Jul. 29, 2003

(54) INJECTION DEVICE AND METHOD FOR ITS OPERATION

(75) Inventors: Birger Hjertman, Vällingby (SE); Markus Ramseyer, Vetendorf (CH); Jiro Arborgh, Umeå (SE); Jonas Fridholm, Bromma (SE); Hans Himbert, Bromma (SE); Carl-Göran Crafoord, Danderyd (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/570,296

(22) Filed: May 12, 2000

Related U.S. Application Data

(60) Provisional application No. 60/172,899, filed on Dec. 21, 1999.

(30) Foreign Application Priority Data

May 12, 1999 (SE) ................................................. 9901736

(51) Int. Cl.[7] .............................................. A61M 5/00
(52) U.S. Cl. ...................................... 604/209; 604/197
(58) Field of Search ............................... 604/110, 131, 604/138, 139, 156, 181, 186, 187, 194, 195, 196, 197, 199, 200, 205, 207, 209, 211, 224, 232, 246, 264, 272

(56) References Cited

U.S. PATENT DOCUMENTS

| | | | |
|---|---|---|---|
| 3,680,558 A | * 8/1972 | Kapelowitz | 604/89 |
| 4,231,368 A | 11/1980 | Becker | |
| 4,444,560 A | 4/1984 | Jacklich | |
| 4,581,022 A | 4/1986 | Leonard et al. | |
| 4,820,287 A | 4/1989 | Leonard | |
| 4,968,299 A | 11/1990 | Ahlstrand et al. | |
| 5,092,842 A | * 3/1992 | Bechtold et al. | 604/135 |
| 5,104,380 A | * 4/1992 | Holman et al. | 604/117 |
| 5,147,323 A | 9/1992 | Haber et al. | |
| 5,425,722 A | 6/1995 | Whisson | |
| 5,514,097 A | * 5/1996 | Knauer | 604/136 |
| 5,584,815 A | * 12/1996 | Pawelka et al. | 604/135 |
| 5,643,214 A | * 7/1997 | Marshall et al. | 604/131 |
| 6,007,515 A | * 12/1999 | Epstein et al. | 604/131 |
| 6,270,479 B1 | * 8/2001 | Bergens et al. | 604/156 |

FOREIGN PATENT DOCUMENTS

| | | |
|---|---|---|
| FR | 2586192 | 2/1987 |
| FR | 2717697 | 9/1995 |
| WO | WO 9531138 | 11/1995 |
| WO | WO 9617640 | 6/1996 |
| WO | WO 9903529 | 1/1999 |

* cited by examiner

Primary Examiner—Manuel Mendez
Assistant Examiner—Mark K Han
(74) Attorney, Agent, or Firm—Dinsmore & Shohl LLP

(57) ABSTRACT

Injector devices and methods for their operation for containers having an opening with or for an injection needle. The container is optionally of syringe type with a barrel of substantially constant axial cross-section. In one embodiment, the devices include a penetration arrangement operable to move the needle from a rear position to a forward position, an injection arrangement operable at least to expel container content through the needle, and a transmission and a switch system allowing manual energy applied to the device to manually operate the penetration arrangement and then manually operate the injection arrangement.

98 Claims, 10 Drawing Sheets

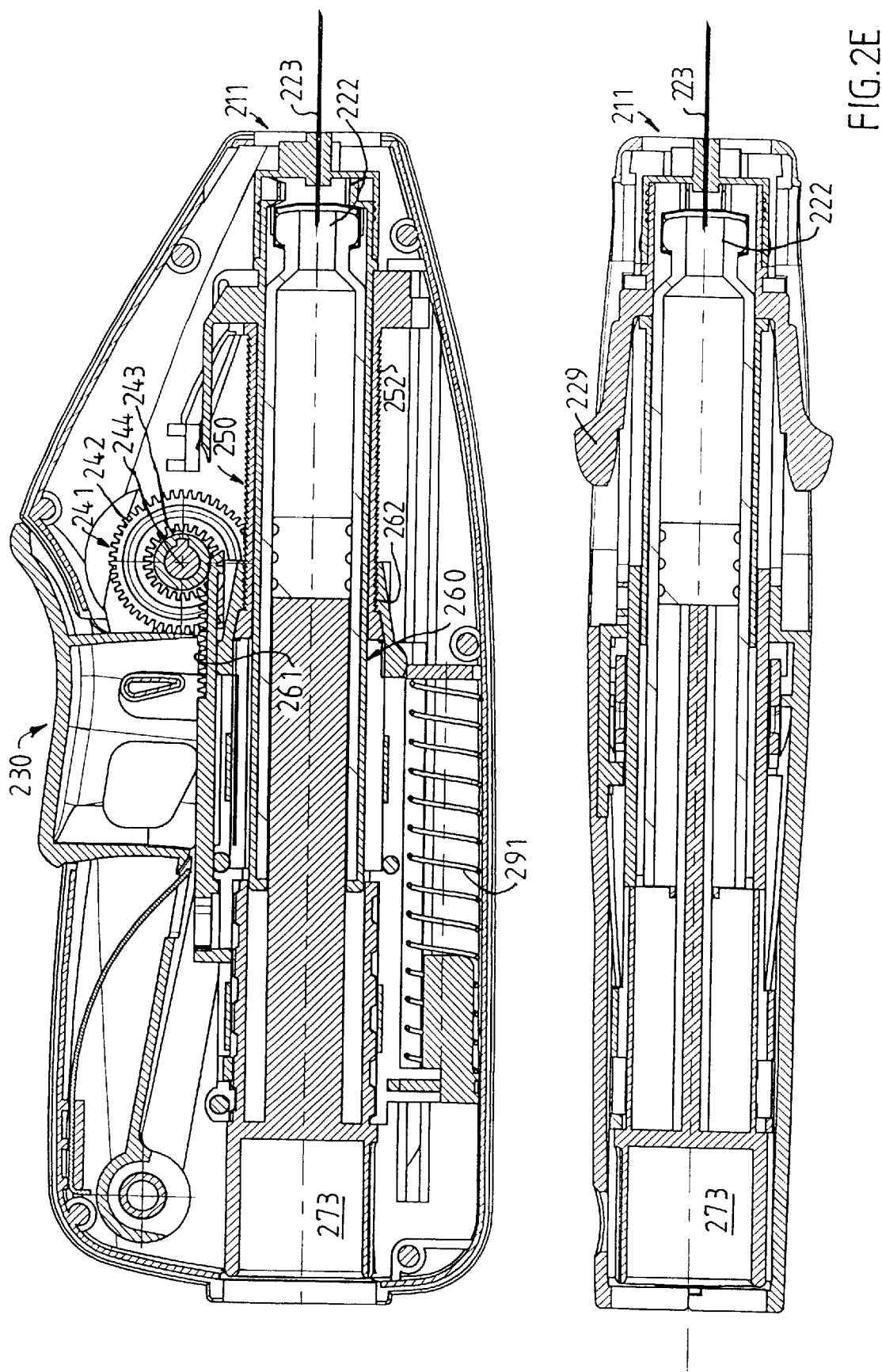

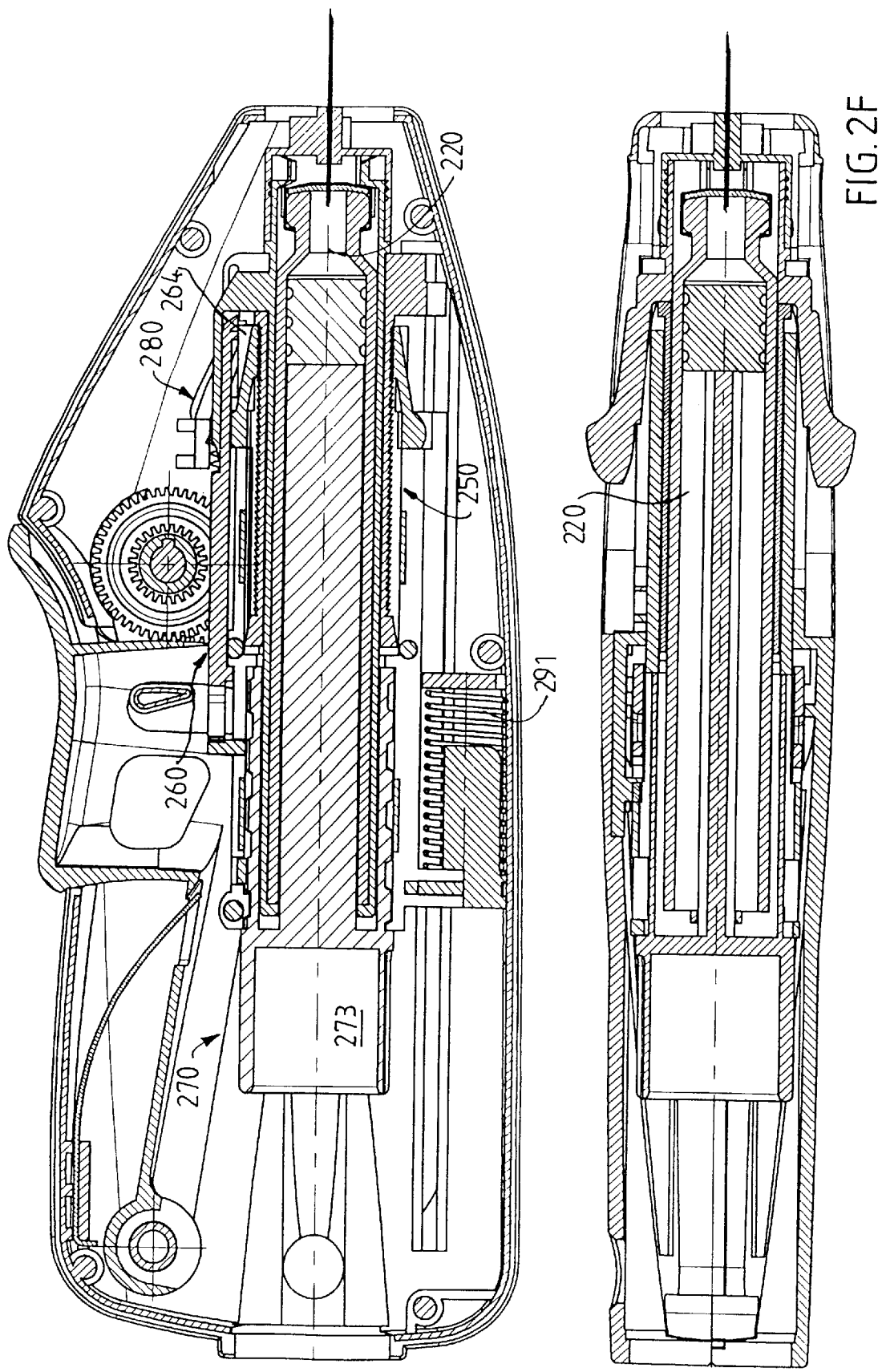

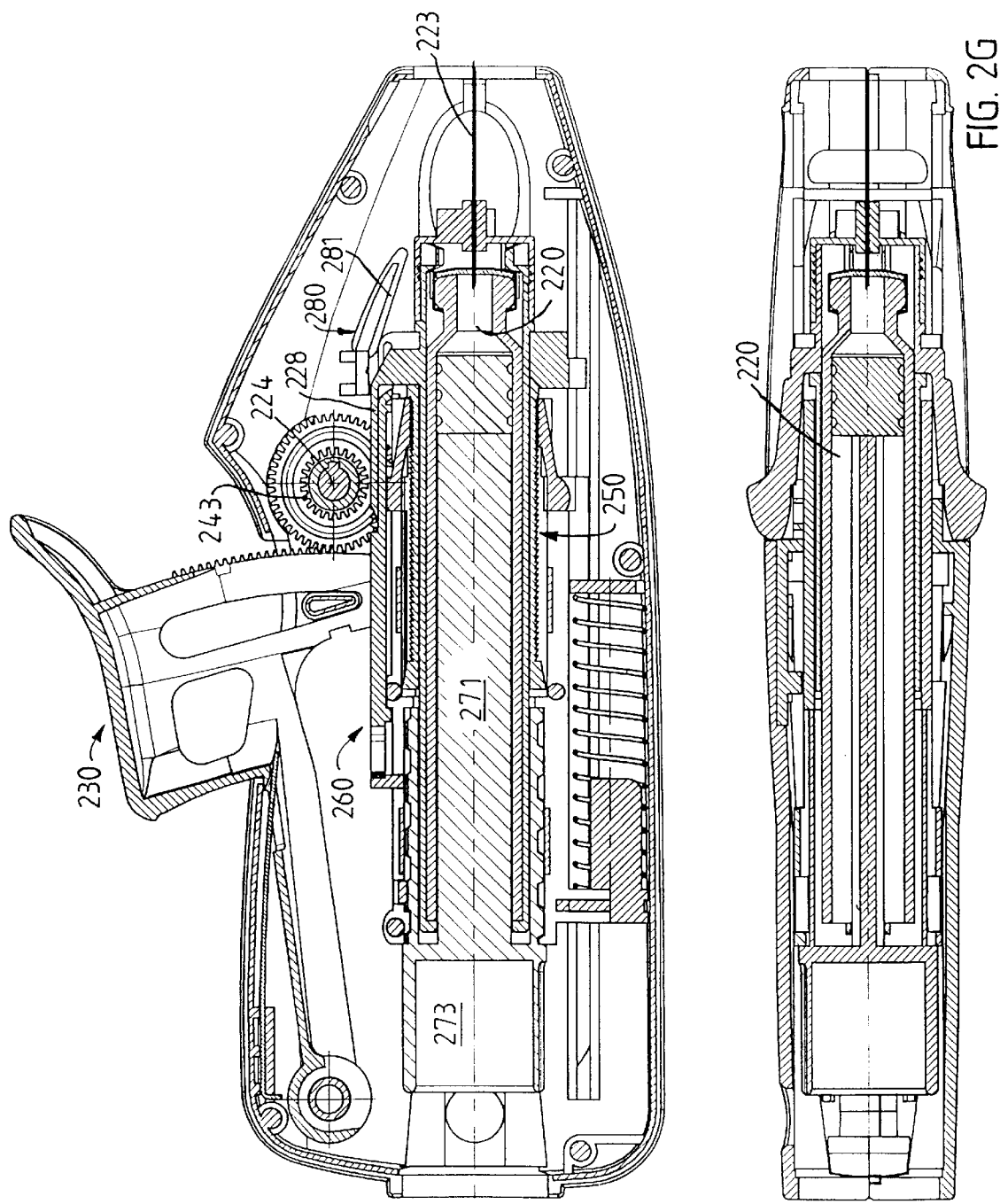

INJECTION DEVICE AND METHOD FOR ITS OPERATION

This application claims the benefit of Provisional application No. 60/172,899, filed Dec. 21, 1999.

TECHNICAL FIELD

The present invention relates to an injector device for containers having an opening with or for an injection needle, the container optionally being of syringe type with a bagel of axially roughly constant cross-section, the opening for the needle being arranged at the barrel front and at least one movable wall, optionally with a piston rod connected thereto, inserted in the barrel, the injector for the containers comprising a) a housing, b) a seat or carrier, arranged for reception of the needle or container and for allowing movement thereof, in relation to the housing, in the axial direction between a rear, needle-covering, position and a forward, needle-exposing, position, c) a penetration arrangement operable to move the needle from the rear position to the forward position, d) optionally a return arrangement operable at least to move the needle in the rearward direction, e) an injection arrangement operable at least to expel container content through the needle and f) at least one control button arranged on the housing and operable to at least initiate operation of the penetration arrangement and/or the injection arrangement.

BACKGROUND OF THE INVENTION

Although simple in principle injection procedures based on syringe type devices with injection needles require mastering of several discrete steps. Before the mere injection procedure some initiation actions may be required. Filling the syringe with medication withdrawn from a reservoir such as a vial may be needed, taking into account the proper dose to be administered. In order to avoid this step in the actual treatment situation it is common to provide pre-filled syringes, in which case, however, a dose setting or selecting step may be needed. In its first movement the syringe piston may need an extraordinary break-loose force after storage to overcome both internal reshaping resistance and an increased wall friction due to adherence or depletion of lubricant in contact points. For storage and shelf life reasons pre-filled syringes sometimes are delivered in dual or multiple-chamber form, requiring an additional mixing step immediately before treatment. De-aeration and pre-ejection are generally needed to remove gas in the vessel compartment and fill out spaces for example at the front sealing, outlet attachments and the interior of the outlet devices or needles. The injection procedure proper can be said to involve the basic steps of penetrating the skin with the needle, performing the injection of the medical preparation and withdrawal of the needle from the tissue. The target tissue may differ in e.g. subcutaneous, intramuscular, intra-cavernosal or intravenous injection and require somewhat different injection techniques, including aspiration steps. Typical problems are full needle penetration into the desired target tissue, injection only after proper location of the needle and full injection of the prescribed dose before the needle is retracted. After injection it is nowadays common to shield or destroy at least the needle to avoid infection transmission by inadvertent secondary needle pricks.

These demands can be met also when using the simplest injection devices, such as the common hypodermic syringe, when in the hands of a skilled operator who also may initiate medically relevant corrective measures in case of accidents and malfunction. However, a general treatment trend is to place administration responsibility on the patients themselves, also in the case of child, elderly and disabled persons. In long-term treatment the patient often develop a certain skill but less frequent administration schemes also exist, often including situations of emergency or patient imbalance. Other unique problems in patient selfadministration, as compared to assistant operated administration, is that less suitable and often strained body positions are required and that apprehended or experienced pain or discomfort may interfere with the medically desirable action pattern. In summary, especially the selfadministration requires more sophisticated devices to facilitate the injection procedure and avoid or reduce risks for mistakes. Patients dependent on daily or occasional administrations also have a legitimate need for convenience and devices discrete enough to be brought around in daily life. Yet it is desirable that such sophistication and convenience is kept simple and inexpensive to allow for widespread distribution and inclusion also in disposable devices.

More or less automated devices has since long existed to enable laymen with limited training performing injections with reasonable safety in critical or emergency situations or to provide an option for patients fearing the needle insertion step. Mechanical automation is provided in common autoinjectors. Typically the user is expected to position the device in proper injection orientation against the skin and operate a trigger button. Stored mechanical energy, e.g. in a spring system, may then perform autopenetration into the tissue, autoinjection of the medical and possibly also automatic needle retraction. Simpler systems may not provide autopenetration but assume the user to make the needle insertion. Generally, once triggering has occurred, either intentionally or inadvertently, the operation sequence proceeds irreversibly. Moreover, the dislocation risks are generally high in mechanical devices due to rebound effects and the forced transitions involved, especially as the forces released may have to be dimensioned for the highest foreseeable operation resistance. Besides being expensive and ungainly, these devices rarely give the patient the experience of full control of the injection procedure and the possibility to halt or correct the injection procedure in case of pain or discomfort.

Automated devices based on electronic or electromechanical principles have also been proposed. The known devices may take advantage of automation principles in several respects, such as the precise and reproducible injection possible with electric motors, motor assisted autopenetration and mixing or reconstitution, cartridge identification, sample analysis, injection data collection and manipulation, dose setting, injector orientation relative gravity for proper mixing or de-aeration etc. Certainly this diversity of possibilities make the automated devices in this class useful in many situations, especially for repeated and frequent use, although the devices tend to be too expensive for broad or disposable use. Again, for patients in favor of personal control the automated functions may be adversely experienced.

On the contrary, simpler manual devices may not at all provide the ergonomic, convenience and safety requirements outlined. A syringe type device for example gives no or little assistance in respect of initiating steps, needle penetration or retraction and requires a cumbersome reverse grip for injection on many body sites and offers no safe sequencing of the various steps involved. Numerous so called "injection pens" have been proposed and marketed, mainly for repeated and regular self-administration, e.g. of insulin or growth hormone, in which multi-dose ampoules are inserted and pre-selected doses delivered, typically by manipulation of an end button. These devices are designed for ease of use in everyday life and facilitate repeated dosing bat do not cure the other problems associated with hypodermic syringes. Also known are injection devices with alternative positioning of control buttons for injection For example, the patent specifications U.S. Pat. Nos. 4,444,560, 4,581,022 and 4,820,287 and WO 96/17640 all disclose a lateral lever with a link arrangement to a piston rod, mainly for the purpose of amplifying the expulsion pressure on viscous dental pastes. Pistol type grips with link arrangements for injection are also known, as exemplified by FR 2717697, mainly for ease of gripping instruments for veterinary mass injection. Also known, as exemplified by FR 2586192, are lateral releasable wheels for fine-tuned movements of needle instruments, mainly for laboratory work. All these solutions, however, are not intended for self-administration and are not optimized for such purposes. For example, no solutions are provided for controlled movement of both the needle and the injection mechanism. Simple devices with means for needle movement as well as injection movements are known, as exemplified by U.S. Pat. Nos. 5,425,722 and 5,147,323, but again without consideration to self-administration, e.g. by requiring different grips for the two actions and without securing proper sequencing.

Accordingly there is a continuing need for simple and inexpensive injection devices able to assist the user in the various handling steps involved, preventing or ameliorating mistakes and offering an ergonomic, convenient and non-traumatic product, especially useful for patients under self-administration. Although the present invention may have a more general utility, it will mainly be described against this background.

SUMMARY OF THE INVENTION

A main object of the present invention is to avoid the disadvantages of known injection devices as described. A more specific object is to provide an injection device able to perform both a needle penetration and an injection step and possibly also a needle retraction step. Another object is to provide a device dependent mainly only on manual energy for operation. Still another object is to provide a device assisting in the initiation steps preceding the injection procedure. Yet another object is to assist in securing a proper injection sequence. A further object is to provide a device able to give amplified or adapted force in various operation phases. Yet another object is to provide a device suitable for delivery of varying doses. Another object is to provide a device compatible with pre-filled syringes of various natures. Still another object is to provide a device suitable for self-administration. A further object is to provide a device ergonomic in use and convenient to handle. Yet another object is to provide a device allowing for minimum pain or discomfort in use. Still another object is to provide a device giving the user control over the injection procedure, yet with maintained safety. Another object is to provide a simple device of low cost, usable as a disposable device. A further object is to provide methods for operating the devices as described.

These objects are reached with the device and method having the characteristics set forth in the appended claims.

By use of an externally accessible control button linked to the device mechanism in such a manner as to allow the operation of the various phases with manual force applied to the button the overall mechanical design can be kept simple and inexpensive. Making at least part of the mechanism movements in the phases at least partially a function of control button position, the patient is given a feed-back from the actions taken, enabling corrective measures. If for example penetration of the needle through the skin causes pain it is possible to slow down needle insertion, halt the operation or select a new target site. Similarly if pain is experienced from the injection phase the injection speed can be reduced, halted or made intermittent. If the phase movements are reversibly dependent of control button position the cause of discomfort can be fully reversed e.g. allowing under the penetration phase partial or fill needle retraction for correction or postponement of the injection procedure. During the injection phase reversal may allow for example aspiration in intravenous injection. Use of the same control button for both the penetration step and the injection step allows the user to perform complete these phases without grip change, allows use of one hand only, reduces the risk for pain caused by grip change dislocation or rocking and eliminates the cause of improper sequencing through inadvertent operation of the wrong control element or double activation of multiple controls. These advantages are consistent with repeated use and operation of the same control button for the various phases. Such an arrangement additionally serves to give the patient tactile feed-back from the progress and completion of phases, thereby increasing patient control and reducing mistake risks. Furthermore it facilitates mechanical transition between phases and functional adaptations to each phase requirement, e.g. allowing different gear ratios between phases or varying response characteristics within a phase. It also facilitates arrangement of simple mechanical lock and release means for mandatory or non-reversible steps in the procedure chain. Mandatory process steps, complementary to patient controlled steps, serve to assist the user in avoiding hazardous sequencing mistakes and to secure proper completion of a phase before the next is enabled and also serve to train and accustom by guidance an inexperienced user to the expected injection program. It has been found beneficial, especially for self-administration purposes, to devise the control button so as to move when operated at least partially in a perpendicular direction with respect to the needle axis, rather than in a coaxial manner and preferably with a side or lateral position relative to the device housing. The control button will be accessible for compression also by the palm, not only by a finger, resulting in a more stable activation with one or two hands, advantages of general importance to avoid no pain but also of particular importance for patients with reduced hand strength or mobility. Furthermore, the device can be held in the palm equally efficient with the needle pointing forwards or rearwards, broadening the operation range and rendering the device equally useful for patient and assistant use. A control button movement different from the penetration direction reduces the risks for any involuntary phase triggering in the preparative actions when the device is pressed against the skin. For a given ampoule length the arrangement also allows for an overall shorter and more handy device. The general design principles outlined are fully compatible with common single or multiple chamber ampoule types in unfilled or pre-filled form and their required initiation steps. If desired the device can include a dose setting arrangement simply by limiting piston stroke length. A needle retraction capability for increased post-injection safety easily flows from a slight modification of the penetration mechanism. All device features can be realized with low cost means permitting its use for most medical purposes including single shot disposable applications.

Further objects and advantages of the invention will be evident from the detailed description hereinbelow.

DETAILED DESCRIPTION

In the absence of explicit statements to the contrary, as used herein expressions like "comprising", "including", "having", "with" and similar terminology shall not be understood to be exclusively restricted to recited element but shall be understood to allow for the presence of further elements as well and shall be understood to cover any element in integral, subdivided or aggregate forms. Similarly, expressions like "connected", "attached", "arranged", "applied", "between" and similar terminology shall not be understood to cover exclusively direct contact between the recited elements but shall be understood to allow for the presence of one or several intervening elements or structures. The same applies for similar expressions when used for description of forces and actions.

Also as used herein the concept "manual" in connection with force or energy applied to the controls of the device shall be understood to mean that the operator applies, directly or indirectly, the force or energy in a manner controlling the procedure under consideration. It shall be understood to include servo arrangements in which force or energy from another source than the operator, e.g. stored energy in a spring or gas or supplied energy, is used in full or in part in assisting driving of the procedure as long as action of the operator determines the proceeding, although servo assistance is mostly not needed or preferred. In contrast to a "trigger" action, which may be an on/off action, the manual action bears, at least partly or over a limited range, a function relationship to position in the procedure affected.

The injector described herein may be used for a variety of purposes within and beyond the medical area and for any type of preparations, such as chemicals, compositions or mixtures, in any container and delivered for any purpose. For reasons outlined the system has certain special values in connection with medical delivery devices where also the design constraints are more severe than in most other applications. For convenience the invention will be described in terms of this application.

Normally the material to be delivered is a fluid and preferably a liquid, including materials behaving as liquids such as emulsions or suspensions. These observations relates to the final preparation whereas other components, notably solids, may be present before final preparation. The nature of container content shall also be understood to include medical in broad terms and to embrace for example natural components and body fluids pre-filled or drawn into the container although most commonly the medical is factory prepared.

The containers usable in the present injectors generally comprises a container for the preparation and an opening through which the preparation can be delivered and a broad range of container types are useful. A needle, cannula or a similar penetration device, all referred to as "needle" herein, should be in fluid connection with the opening, e.g. by being arranged on, at or with a conduit to the opening Unless a container type in itself includes means for ejecting its content a pimp mechanism may additionally be needed to be further explained. Syringe type containers are preferred for use in the present injector and shall be understood in broad terms and can generally be said to include a barrel having a front part and a rear part defining a general axis, an outlet for the preparation, typically comprising a liquid in broad sense, arranged at the front part and at least one movable wall arranged at the rear part, a displacement of which wall causes the preparation to be moved towards or expelled through the outlet, thereby including an inherent pump mechanism. Barrel shape and movable wall have to be mutually adapted. The barrel of for example glass or plastic may have a substantially constant internal cross-section, with a similarly constant barrel axis, between front and rear pails giving a generally tube-shaped barrel, and most preferably the cross-section is of the common circular type giving a substantially cylindrical barrel. The movable wall is then preferably a substantially shape-permanent, although possibly elastic, body sealingly adapted to the internal barrel surface and preferably of the piston type. At the front end of the barrel the needle is arranged and the invention is preferably used with containers wherein the needle axis is substantially parallel with barrel axis, and most preferably concentric therewith, resulting in that the penetration and the injection movements are substantially parallel. Within these limits and preferences a broad range of syringe type containers can be used with the present injector device, such as ampoules, cartridges, carpoules and syringes. The container need not have a separate piston rod but it is preferred that the injector mechanism can act more or less directly on the container movable wall, although it is fully possible that the container has a piston rod, in the sense of a part protruding from barrel rear end, on which the injection mechanism can act for movement of the piston, since many standardized devices are so designed. The injector can with preference be used with standard container types, e.g. as defined in DIN and ISO standards. Also usable are dual or multi chamber container types, known e.g. for preparations demanding a mixing of two or more components or precursors before administration. The components are kept separated by one or more intermediate walls of different known designs, which walls divide the barrel into several chambers, sometimes placed parallel along cartridge axis but most commonly in stacked relationship along the axis. Unification of the components may take place by breaking, penetrating or opening a valve construction in the intermediate walls. In another known design the intermediate wall or walls are of the piston type and flow communication between the chambers is accomplished by moving the piston to a by-pass section where the interior wall has one or several enlarged sections or repeated circumferential grooves and lands or piston deforming structures in a manner allowing by-flow of rear chamber content into front chamber at displacement of the rear movable wall. The chambers may contain gas, liquid or solids. Generally at least one liquid is present. Most commonly in pharmaceutical applications only two chambers are present and typically contains one liquid and one solid, the latter being dissolved and reconstituted during the mixing operation. For these types of containers it is possible both that the mixing or reconstitution step has already taken place when the container is placed in the injector or that means are provided within the device for unifying the chamber contents before the actual injection process is started.

Positional and directional statements for both the needle, container and the injector, such as "axial", "front" and "rear", shall be understood with reference to tie needle, although when the needle and container are arranged to move together as described for syringe type containers it is equally true to refer to the above described parts of the container.

The needle may be connected to the container front in any manner, e.g. in the known manners of being permanently fixed by gluing, fusing etc. or by an attachment such as a luer connection, threads, threaded splines, snap-on connections or combinations thereof. The container front should be adapted to the attachment type selected, e.g. being of fusible material, being supplemented with a membrane that can be pierced or ruptured or having a front valve or by-pass arrangement. It is clear that the needle either may be connected by the manufacturer for best convenience or by the user prior to injection, e.g. to assure the user maintained sterility, to allow selection of needle type or gauge value or for repeated use of the device. Also in accordance with common practice the needle may be covered by a sterility preserving needle shield to be removed immediately prior to use. Use of standard needles, syringe fronts and attachments is preferred to maintain low costs. However, modifications may be used to achieve special advantages. As in the aforementioned U.S. Pat. Nos. 5,425,722 and 5,147,323 devices the needle need not be attached directly or rigidly to the container but with any other fluid connection. This e.g. in order to allow needle movement independent of the container, which may then be non-movable in the housing, and restrict movements to the needle proper in e.g. the penetration and needle retraction steps, simplifying the mechanism of the device. Unless otherwise indicated this option shall be considered included in the movable seat or carrier concept to be described. In this case the container need not be of syringe type but any container type can be used and injection performed by any pump mechanism, such as container squeezing, positive displacement pumps, e.g. piston/cylinder types, based on aspiration from the container followed by ejection, peristaltic action etc.

The injector device comprises a housing, which shall be understood in broad sense and basically as a point of reference for positional and directional statements for other parts and components. It is preferred, however, that the housing also actually enclose at least the mechanisms of the device and leave exposed mainly the parts that should be accessible to the user, mainly the control button but also auxiliary parts such as dose setting, alarm, arming, triggering and cocking controls. The container can be attached to the housing in such a manner that it remains exposed, although it is preferred that the housing also confines the container, preferably also the needle until penetration is initiated. The housing may be designed to be partially or fully openable and/or closeable to access or close its interior, which may be facilitated by any known separation or openable arrangement, e.g. threaded or hinged parts, possibly with reversible or irreversible locking means. Reversible locking may be used to access the device interior e.g. for adjustment or control or to allow simple insertion or replacement of containers, e.g. to permit reuse of the device, for loading of selected or varying preparation types or doses. As indicated it is often preferred to use the device as a disposable in which case it is preferred to factory load it with the container and a simple closure arrangement is still of value for rational assembly in manufacture. For safety and security reasons an irreversible closure may be of value to prevent any tampering with the used container and needle. In broad terms the housing shape is not critical for the basic function of the device but may influence its ergonomic and convenience properties. The overall shape of the housing can take a variety of shapes depending on among others the internal component layout. As indicated the housing incorporates at least the container and the transmission mechanism between control button and container. As in the prior art most of the mechanism parts can be arranged axially behind the container in which case a minimized housing can take an elongated form. The control button can be designed for axial depression. For the several reasons outlined it is preferred to design the control button for lateral movement relative container axis and for this option it is preferred that at least the control button is located at least partly lateral to container axis and preferably between the container ends, and preferably also at least part of the mechanism is similarly located between the control button and the container. A minimized housing embracing these parts can then be given an axially shorter but laterally wider shape and if said lateral housing, excluding button, extension is considered as "height", the axial extension as "length" and the dimension perpendicular to these two as "width", it is preferred that the maximum height to maximum width ratio is larger than 1, preferably larger than 1.5 and most preferred larger than 2. The maximum length to maximum height can often be kept less than 4, is preferably less than 3 and most preferably less than 2.5. The overall shape described has been found ergonomically suitable, structurally rigid and easy to manipulate and assemble in manufacture.

The injector further comprises a needle seat, the minimum requirement of which is to allow at least the needle, and preferably needle and container when rigidly connected, to be axially movable in relation to the housing, for penetration purposes, between a rear position and a front position, movement between which positions is used for penetration. The distance traveled between the positions should correspond at least to the desired penetration depth and, when the needle is hidden within the housing before the penetration step, also the distance needed for internal travel to expose the needle tip. The needle seat may comprise guiding structures fixed in relation to the housing, securing the desired needle path, or may alternatively or additionally comprise a carrier movable in relation to the housing and in which the needle or container is retained. Depending on the needle seat design selected the penetration mechanism to be described may act directly or indirectly on the needle, the container or the carrier for propulsion of the needle during penetration and possible needle retraction. Optionally the actual penetration depth is adjustable, e.g. in the seat path or in the penetration mechanism. Alternatively the depth is adjusted by the needle length selected.

As said the device shall incorporate arrangements for at least a needle penetration movement and an injection movement for the container content. Preferably the device also comprises arrangements for needle retraction. It is also preferred to include features assisting the user in the injection initiation steps to be described.

With some similarities to corresponding capabilities in autoinjectors, penetration and injection may take place concurrently, e.g. in simple devices or for the intentional purpose of allowing for an over depth distributed injection. Normally it is desirable to limit injection until the needle has reached or is close to its target location. This feat can be obtained with a force system acting on movable wall or piston rod for both purposes, relying for sequencing on the normally lower needle penetration resistance than fluid ejection flow resistance. Yet it is difficult to avoid at least some leakage during penetration but above all, in case the penetration movement is prevented or jams, injection will entirely fail with preparation expelled on the skin or at improper depth. Hence it is preferred to apply penetration force directly or indirectly on the needle or container, which requires some control mechanism disabling injection force application during most of the penetration phase and enabling injection force only after proper penetration. A needle retraction step can be performed manually, but is preferably made at least semi-automatically in order to guarantee safe hiding of the needle, which can be made e.g. in a manner known per se in which stored energy, typically stored during the penetration movement in a weaker return counterspring, acts to push the syringe back into the injector after completed injection. Again, this function may need a control mechanism enabling action of the return spying only after completed injection, normally accomplished by separation of the penetration and injection forces from the syringe at a certain forward extreme for the piston or piston rods freeing the return spring for action.

The penetration movement shall take place by use of manual energy applied to the control button and a penetration transmission may be needed to transfer the force between the control button and the needle, possibly via container or carrier, as the case may be, and preferably on or via the container barrel for reasons mentioned. In principle any conventional transmission means can be used, e.g. electromechanical, such as electric motors or solenoids, hydraulic, pneumatic etc. system but preferably mechanical means are utilized for simplicity. The transmission may take a variety of forms depending on the button position and mobility. If for example the button is positioned on the housing at the axial extension of the container or needle axis the transmission can be a more or less rigid connection if the button mobility is towards the front or a screw and nut transmission if the button is arranged for rotational movement around said axis. Preferably the button is arranged for movement with at least a component perpendicular to the needle axis, most preferably for needle ejection when moving the button towards the housing, e.g. as a more or less guided translational movement along such a button path or as a rotational movement around a rotation axis, preferably a rotation axis along the housing width direction in which case the push area of the button can be located behind, but preferably in front of, the rotation axis. As said the button is then most preferably positioned lateral to the needle axis but between container end boundaries. In these cases it is preferred to use a transmission able to redirect the force applied to the button, which can be done with any known such transmission arrangement, e.g. wire or belt type arrangement, a link arrangement such as a limb and joint system, a lever arrangement and preferably a wheel, preferably toothed wheel, system in which the button movement rotates the wheel for propulsion of the needle, preferably via a toothed rail. If desired any transmission may contain force transforming parts to increase, decrease or vary the force during the penetration stroke. Known such means can be used, e.g. by adaptation of gear ratios, lever degrees, knee elements or use of cam surfaces. Also the control button itself may be used for leverage, e.g. if hinged and by adaptation of pressure point to force extraction point for the transmission. Generally the penetration step requires only small forces due to the little insertion resistance in soft tissue and it is preferred for good patient control and feed-back that the button stroke length is not too short during this step. Preferably the finger movement on the button to needle movement length ratio is larger than 0.1, preferably larger than 0.2 and most preferably larger than 0.5. Preferably the ratio is less than 10, preferably less than 5 and most preferably less than 1. It is desirable that a definite stop for button movement is provided at full predetermined needle ejection, e.g. by a stop surface arranged anywhere in the chain between button and needle.

The injection movement may take place automatically during or after the penetration movement, which may serve the purpose of reducing the number of step to be performed by the patient or when injection pain is unavoidable e.g. due to irritating compounds in the injected preparation. This result will be obtained if the force application principle is used in which penetration force is applied to the container movable wall, as described, under continued operation of the control button. Alternatively non-manual stored energy may be applied to the injection mechanism, e.g. by a spring or gas pressure system, preferably to be released at the end of the penetration movement, which may require an enabling mechanism at this point similar to those used in autoinjectors, e.g. a structure on the housing releasing a lock between the stored energy drive and the movable wall at a point in the housing corresponding to completed penetration. For reasons mentioned it is preferred that also the injection movement takes place by use of manual energy since it is desirable to give the patient feedback from and control over the injection for corrective measures or speed control as pain or discomfort may result form the injection, especially at larger injected volumes. After use of the control button for penetration such manual injection may take place by use of a separate injection control, for which purpose any known injection mechanism or described transmission may be used. It is, however, preferred to use the control button also for the injection procedure. A transmission is then needed between the control button and the container movable wall, similar to that for penetration, but acting on the movable wall, and any of the transmission principles described may be used also for injection. An entirely separate transmission for the injection can be used but preferably the transmission comprises common parts for the two purposes and most preferably they differ substantially only where necessary, in particular in respect of details for shift between the phases and adaptations for each phase. In the latter regard it might be of interest to adapt the force requirements since these are higher for injection than for penetration. This can be done by increasing the gear or lever ratio. Preferably the finger movement on the button to movable wall movement length ratio is larger than that for finger movement versus needle movement used under penetration. For injection said ratio is preferably greater than 0.2, preferably larger than 0.5 and most preferably larger than 1. Preferably the ratio is less than 20, preferably less than 10 and most preferably less than 5. In case the finger movement tends to be inconveniently long it is possible and preferred to allow for repeated operation of the control button until emptying of the container is complete.

For the simplest operational options described, e.g. when acting on the container movable wall and when using a single button stroke for both phases, it might not be necessary to include any switch system for enabling and disabling respectively or redirecting the forces applied to the control button. To reach most of the preferred capabilities described, however, it is preferred to includes such a switch system. A first desired switch function is a phase shift system allowing the force applied to first act on the needle, directly or indirectly e.g. via container barrel or a carrier, for penetration and then act, directly or indirectly, on the movable wall for injection. A second desired switch function is a reconnect system allowing repeated operations of the control button. These desired functions are to some extent mutually dependent, as for example press and release actions on the button can be used to accomplish a phase shift, e.g. at a certain position for the button movement although it is preferred to use other means than the button, and all possibilities and combinations cannot be enumerated of described in detail. In broad terms phase shift can preferably be made at a certain relative axial location between needle and housing, e.g. corresponding to completed penetration stroke or preferably slightly before to avoid too high tolerance demands on the shift mechanism. Physically the shift can preferably be made by using a structure, with substantially fixed location with respect to the housing, to redirect or unlock the force applied for action on the movable wall, e.g by deflection, rotation or any other mechanism, or preferably by applying force at a constant location, preferably by a wheel, where automatic shift takes place when penetration a movement is completed, e.g. by having the wheel first act on a surface for penetration and then changing over to a surface for injection when penetration is completed, which principle also allows for change of gear ratio. For several reasons, e.g. to secure proper sequencing and avoid inadvertent withdrawal, to facilitate adaptations for later needle retraction and to indicate penetration completion to the user, it is preferred to provide a lock to hold, at least temporary, the needle in the front position, which can be made by any lock structure, e.g. a hook structure, preferably biased for automatic engagement in that position and possibly designed for, or supplemented with, a tactile or audible confirmation of penetration completion. The lock may be permanent, e.g. if no needle return function is present, or releasable with features of the internal mechanism or even manually if used for needle or container front access.

A properly designed phase shirt system, preferably by structures other than the button, as above offers broad freedom for design of the reconnect system and movement pattern for the control button. It is possible to use a single button stroke for both penetration and injection, e.g. to minimize patient actions or for small injection volumes or penetration depths or to allow for aspiration of liquid and in this case no reconnect system need to be present. Among others in order to give the patient phase dependent feedback, arrange for phase dependent adaptations or avoid too long button strokes, it is, however, preferred to use at least two actions on the button, preferably at least one for penetration and at least one for injection, and possibly several strokes within a phase, especially the injection phase as said. This can be accomplished by using the button as part of the phase shift system, e.g. by using the end of the first button stroke for phase shift and further movement of the button for injection. It is preferred, however, to use the phase system principles mentioned other than the button, which permits a more general design of the reconnect system. A general reconnect system may allow two-way button movement. It may allow force to be applied to the transmission during movement in both directions but is preferably designed to be idle in one movement direction, preferably idle when moved away from the housing, for best convenience. Mechanically any known one or two way means may be used, such as clutch, centrifugal or friction based mechanisms, pawl and ratchet mechanisms or preferably a wheel with releasable axis. With any such design the button movements can be repeated freely, e.g. allowing patient mistakes or action individuality, while the phase shift system secures the proper phase sequencing. Reversible phase action is possible. It is for example beneficial that the needle movement during penetration can be reversed in certain situations, e.g. to allow interruption and selection of new injection site if pain is experienced or to allow exposure of the needle or container front for inspection or for needle attachment. Reversible penetration can be obtained e.g. by having a force bias in the needle reverse direction, e.g. a needle retraction spring. During injection a several stroke pumping action is automatically achieved with the general reconnect system, more safely though if rearward movement of the container is prevented, e.g. in the embodiments with fixed container, if not rearward biased or if locked in the foremost position as described. As an additional safety measure during the injection, especially when several stokes are needed, rearward movement of the movable wall can be prevented, e.g. by allowing forward movement only of the parts acting on the movable wall, e.g. by inclusion of a friction element, a one-way ratchet mechanism or by similar means. It is also preferred to bias the button itself towards one of its positions, preferably towards the button start position such as the outer distal position relative the housing, which can be done with simple and inexpensive means, such as a spring in metal, elastomer or plastic.

For reasons stated a needle return function is preferably included in the injector. With respect to force application for needle retraction similar considerations apply as for penetration, i.e. the force can be applied directly to the needle or its attachment, to container barrel or any carrier for these parts. The needle may be retracted by application of manual energy, e.g. to give the user control also over this action. A separate control may then be arranged, allowing a simple construction and a simple connection between control and needle. For convenience it is preferred to use the control button also for needle retraction, especially if this step shall take place in connection with the injection procedure and for withdrawal from the tissue. A transmission and button reconnect system of principles similar to that for penetration and injection may then be needed. Needle withdrawal from the tissue is rarely a painful task, however, that necessarily need full manual control. For this and other reasons it is preferred make needle retraction at least partially automatic. The function may be semi-automatic in the sense that after a mandatory manual triggering needle retraction proceeds automatically, preferably by release of stored energy, e.g. in the known manner of arranging a return spring biased for rearward needle movement, commonly compressed during the needle penetration step The triggering may take place via a separate control for this purpose but preferably the control button is also used as trigger for needle retraction. The control button may release the needle retraction when it is released after the injection but it is preferred that an additional, repeated, operation of the button is used. For highest safety and ease of operation needle retraction can be fully automatic in the sense that this step follows at a particular point in the injection procedure, without any manual triggering action from the user. The procedure point is preferably when the expulsion of preparation is finished and hence the injection phase completed, which may be when the movable wall bottoms out, in case of container complete emptying, or at a certain movable wall position, in case of partial emptying, the latter useful mainly when the dose can be set or adjusted or for repeated injections from multi-dose containers. Expressed in another way, the movable wall arrival at the predetermined position is taken as the triggering event for needle retraction. Mechanically any part of the injection transmission including the button, which parts has a determined positional relationship to movable wall position, can be used as internal trigger, e.g. to enable release of stored energy for example by unlocking a return spring lock. In case a lock is provided to retain the needle position after penetration, in the preferred manner described earlier, with preference such a lock can be used for enabling of a return spring for action. In case it is desirable to disable the device permanently after needle retraction, e.g. for single use disposable devices, arrangements may be provided to lock the needle in the retracted position in a non-releasable manner, e.g. by any known means, again anywhere in the transmission chain. As part of this feature, or additionally e.g. to indicate the used status to the user, the control button can be locked against further movements, preferably in its compressed position to conserve space. In case no needle retraction function is present, but other safety precautions are relied on, e.g. incineration, for destruction the non-releasable locking can take place after the injection phase.

In order to allow setting of the dose to be ejected, e.g. for partial or repeated injection, a dose setting mechanism can be included. Since the dose setting generally takes place before the actual injection procedure is initiated and without restrictions in device position, controls for this purpose can be arranged more freely than the control button. Although it is possible to include adjustable displacement limitations acting on the movable wall as such, it is generally preferred to provide such limitations for action on the parts earlier in the injection chain. They may be arranged in the control button or anywhere in the injection transmission, but it is preferred to provide separate such limitations. Any common means, known as such in for example injection pens, can be used. If the last part of the transmission affecting the movable wall or the piston rod as the case may be, is regarded as a "plunger" arrangement it is for example possible to use an adjustable stop surface for the plunger arrangement, an adjustable space for plunger dead run relative to the movable wall or a combination thereof. It is possible that the injection stroke length, or combined stroke lengths, for the control button varies for different dose settings but preferably dose setting mechanisms are selected in which the stroke lengths are kept constant and independent of the dose setting.

It is also preferred to include in the device features facilitating initiation steps preceding the actual injection. It is possible to deliver the device without any container or needle for later attachment of these parts and in order to facilitate attachment the container site may comprise an attachment such as a push lock, bayonet, threads or any other fit. It is also possible that the needle is pre-mounted on the container but commonly it need to be connected immediately prior to use or allow for replacements and in most cases a needle shield need to be removed prior to use and in all these instances the needle attachment site, most often the container front, need to be accessible to the user. Possibly the device has a compartment for needle storage before attachment. In case of dual or multiple chamber cartridges initiation may require an initial movement of the movable wall to unify and mix chamber contents and although this step may be performed before container attachment to the device it is preferred to allow for this when attached to the device, e.g. allowing the plunger arrangement to be initially movable against the movable wall, e.g. by a temporary release from the transmission, but preferably by making the container axially movable against the plunger when stationary in the housing and most preferably by threaded attachment permitting cautious displacement of the movable wall as described e.g. in U.S. Pat. No. 4,968,299. An initial displacement of the movable wall is also needed to perform de-aeration and pre-ejection, which movement may take place with similar means as for multiple chamber containers. Any initial movement of the movable wall may require high break-loose forces. For any or all of these actions it is beneficial that at least the container front is accessible to the user, which can be arranged for by utilization of the penetration mechanism to at least partially make the penetration movement and preferably temporary lock this position to resist the manipulation steps applied. It is also possible and often preferred to make at least the device front part open or openable through removal, hinged door etc. The displacement of the movable wall for the above mentioned initiation purposes may take place by manually pushing the plunger or the container towards each other in axial direction. It is, however, preferred to arrange for an assisting leverage or gear ratio, for example to increase force for break-loose, reduce speed in mixing or keep the initiation movement short in de-aeration and pre-ejection. Any known leverage principle can be used but a preferred arrangement is use a hinged door for the device front, the closing of which causes the container to move rearwards, preferably under force amplification and preferably under displacement of the movable wall forwards, such as when the wall is substantially stationary in relation to the housing. After closing of the door the needle is preferably hidden within the housing and it may be beneficial to arrange the door so that it cannot be at least fully closed unless the needle is properly attached and further so that the door is permanently and irreversibly locked, and possibly also arranged to block any further change of a dose setting control if present. A door may additionally serve to influence the possible control button movements, in particular to enable or disable movement thereof. For example the button may be inoperable until the door has been fully closed, with any of the additional functions mentioned above, either by being disconnected from the transmission or by being held stationary in a given position by blockage of the button or the transmission. All these arrangements serve to secure a proper sequence of actions and reduce the risks for mistakes or misuse.

The methods for using the device follows from the descriptions made of structures, functions and objects. Below a summary of preferred actions. Any door or closure over the device front is removed or opened. If the container is not pre-assembled in the device housing the operator inserts the container and possibly connects it to attachments provided. If the container is a dual or multiple chamber device mixing operation may be undertaken before attachment to the device but is preferably made when attached or during attachment to the device, preferably by actions involving an axial displacement of the container towards a plunger arrangement in rest abutting the movable wall. Unless a needle is already in place the operator mounts a needle on its seat and possibly removes any needle shield present. The needle is pointed roughly upwards and the movable wall is moved forward to expel air and possibly eject a small preparation amount to assure proper function. Preferably the wall is moved forward by displacing the container rearwards against a plunger arrangement and most preferably by closing a hinged door arranged to also displace the container rearwards. Such displacement may be levered so that the closing length exceeds the container displacement length. Preferably the closing also acts to enable the control button for action. The steps performed should secure that the needle is now hidden within the device. If applicable a dose setting operation may take place at any point up to now. The control button is operated to perform penetration movement to bring the needle to an exposed position. This is preferably made in a single step, without repeated action on the button, and preferably by pressing the button towards the housing, a movement preferably having at least a component perpendicular to the axial direction. The exposed needle may now be inserted into a target object, e.g. human or animal tissue or any other material or device e.g. for laboratory use, but preferably the device front is placed against the receiving object beforehand so that said insertion takes place as a result of the penetration movement. Preferably the needle or container is locked at the penetration end position and it is preferred that an audible or tactile signal is issued, by the locking arrangement or otherwise, to confirm completed penetration to the user. A injection step may now be performed. This can be done with a continued movement of the control button but preferably the button movement pattern is changed for injection, preferably involving release for return to a start position and most preferably so that a new movement from the start position performs the injection. Several injection strokes can be made with the button during injection, especially for larger injected volumes or as an adaptation for weak persons. Completed injection may be sensed as a stop for the button when the movable wall reaches the container end or at abutment of stop surfaces arranged in the transmission. Preferably a needle return step is now performed, either automatically or triggered by the operator. Triggering may be made by a separate trigger, by release of the control button or first when the button is again operated. Although the needle may be removed from the object before the needle return step it is preferred that removal takes place as a result of the needle retraction step.

Although the above method steps have been described as a sequence of given order it is within the spirit of the invention that other sequence orders may be used unless specific statements to the contrary are given.

Further details of the invention will be evident from the description of specific embodiments with reference to the drawing figures.

SUMMARY OF DRAWINGS

FIG. 2A to 2G show a detailed embodiment of an injector in several operational phases. FIG. 2A is an exploded view of the device components and FIGS. 2B to 2G show in height and width sections the various operation phases.

DESCRIPTION OF DRAWINGS

Figure 1A:
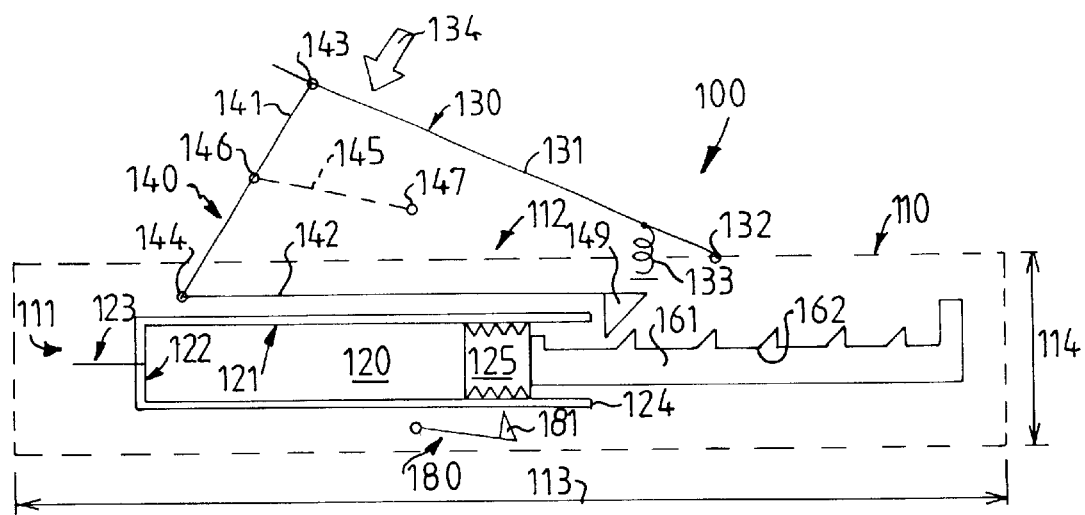
FIGS. 1A and 1B illustrate schematically in two states an injector having a transmission incorporating a link arrangement for transmitting force applied to the control button.
Figure 1B:
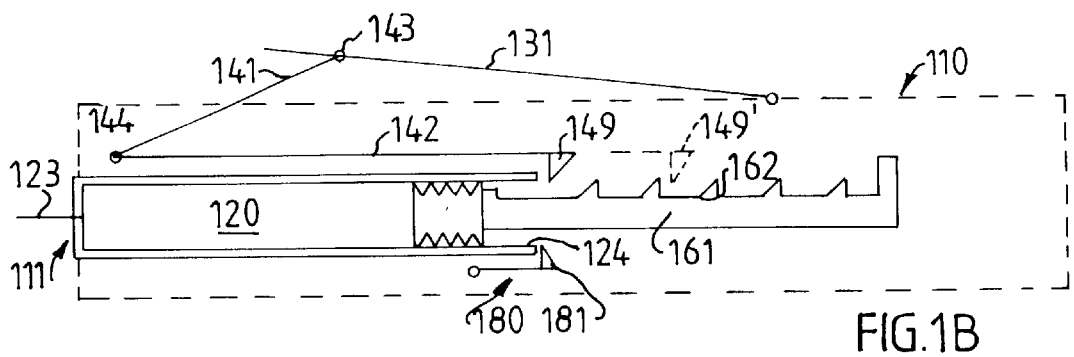

FIGS. 1A and 1B illustrate schematically an injector having a transmission incorporating a link arrangement for transmitting force applied to the control button. In FIG. 1A the schematic control button is in an initial position and in FIG. 1B the control button is a depressed position The injector, generally designated 100, comprises a housing 110 indicated in phantom lines, with a front opening 111 for needle exposure and a side opening 112 for the control button. The housing has an illustrated length 113 and height 114 and a width (not shown) perpendicular to the height and length. A syringe type container 120 is arranged in the housing and comprises a barrel 121, a front 122 with needle 123, a rear barrel end 124 and a movable wall 125 in the form of a piston inserted in the barrel. The container 120 is arranged axially movable in the housing 110 between a rear position, shown in FIG. 1A, and a forward position shown in FIG. 1B. A control button, generally designated 130, can be said to include a manually accessible part 131, pivoting around an axis 132 extending in the width direction of the housing and being biased towards the initial position, most remote from the housing, by a button spring 133. By application of manual force directed towards the housing, illustrated by arrow 134, the button part 131 can be moved to the compressed position shown in FIG. 1B against the force of button spring 133. It should be noted that the manual force applied to the button in the direction of arrow 134 has a component perpendicular to the container 120 axis although the force is not flatly normal to said axis. Furthermore the angle relationship changes somewhat between the positions shown in FIGS. 1A and 1B due to the pivoting movement of the control button. It should also be noted that the control button is located lateral to, and not coaxial with, the container axis and with a pressure point 134 between the axial ends 122 and 124 respectively of the container 120. A transmission 140 can be said here to include a link arrangement comprising a first arm 141 and a second arm 142, the first arm 141 in one end being connected to the control button in a first elbow joint 143 and in the other end to the forward end of a roughly axial second arm 142 in a second elbow joint 144, the joints allowing rotational movements in the plane of the FIGURES. The first arm is arranged so that the second elbow joint 144 moves forwards when the control button is depressed in the allow 134 direction. In doing so it brings the front end of the second aim forwards and, as the second arm is arranged substantially axially, also its rear end will move forwards. In order to secure the desired movement pattern, e.g. avoid rearward collapse of the first arm, guides may be provided, either guiding structures on the housing e.g. in the form of rails or slits or, as common in link arrangements, additional links as illustrated in phantom lines by a third arm 145, attached for rotational movement at a third elbow joint 146 to the first arm and having its other end attached to the housing at a fourth joint 147 for rotational movement. It is clear that the arrangements described transforms the perpendicular force component applied to the control button into an axial movement for the rear part of the second arm at which end a pusher structure 149 is arranged, which pusher is illustrated as a pawl having a flat driving front surface and a tapering overriding rear surface, for action on the container. The transmission parts so far described can be said to be common for the penetration arrangement and injection arrangement of the device. Further details of the penetration arrangement in this embodiment is simple and can be said to include adaptations between the pusher 149 and the rear barrel end 124, allowing the pusher to displace the container 120 from the rear position to the front position. Further details of the injection arrangement can be said to include a plunger 161, arranged to act on the movable wall 125, having teeth 162, illustrated as ratchets with rear flat surfaces and overriding tapering front surfaces, arranged for cooperation with pusher 149. As will be described the pusher 149 and teeth 162 can also be said to act as the switch system for the device, allowing the pusher first to act on the barrel 121 for penetration purposes and then catch the plunger teeth 162 for injection purposes. The pusher 149 and multiple teeth 162 can also be said to act as a reconnect system for the device, allowing the control button to be repeatedly depressed and released for successive injection movements. Also schematically illustrated is a lock 180, having a hook part 181 being biased towards the container barrel 121 and positioned to move behind the barrel end 124 at the end of the penetration movement and prevent rearward movements during subsequent steps.

FIG. 1A illustrates the initial state of the device parts. Applying force to the control button 130 in the direction of arrow 134 will rotate button part 131 around axis 132 causing first arm 141 to rotate around first elbow joint 143 under displacement of second elbow joint 144 forwards, thereby bringing also the second arm 142 with rear pusher 149 forwards. In the first movement of this kind pusher 149 will engage rear barrel end 124 and move container 120, including the plunger 161, forwards, thereby exposing needle at housing 110 front opening 111. At the end of this movement the lock 180 hook part 181 will engage rear barrel end 124 to prevent rearward movements of the container. This state of the device is shown in FIG. 1B At release of the button 130 the spring 133 will move it back into its initial position shown in FIG. 1A but lock 180 will prevent the container from moving back. Instead the rearward movement of pusher 149, resulting from control button return to its initial position, will override one or several teeth 162 of plunger 161 by cooperation of the tapering surfaces on both pusher and teeth, for engagement of the plunger 161. Accordingly the parts involved acts as a switch system, permitting button release to perform a phase shift from penetration action to injection action. Next the control button is depressed again and the resulting forward movement of pusher 149 now brings plunger 161 forwards by action on teeth 162, schematically illustrated in FIG. 1B by dashed lines at 149'. If necessary or desirable for the desired dose to be injected the button can be released and again depressed to engage further teeth 162 rearwards for repeated injection strokes. Accordingly the pawl and ratchet type of mechanism provided by the pusher 149, the rear barrel end 124 and multiple teeth 162 will act as a reconnect system, allowing repeated action on the control button.

Figure 1C:
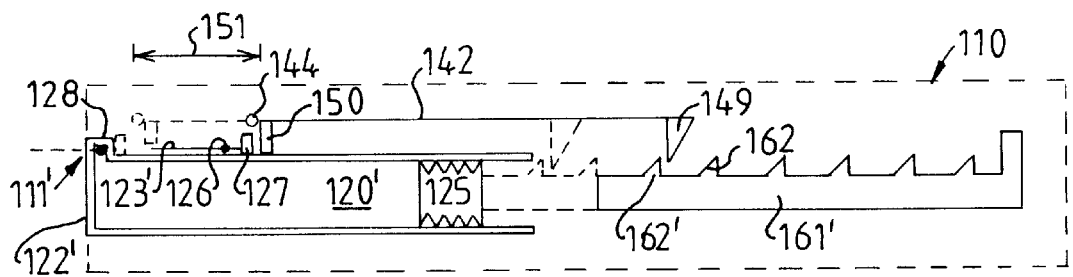
FIG. 1C illustrates a modification having a stationary container and movable needle.

FIG. 1C illustrates schematically a modification of the embodiment of FIGS. 1A and 1B wherein the container is stationary in the injector and the needle makes its movement independent thereof. In the drawing only the second arm 142, the second elbow joint 144 and the pusher 149 of the link system is repeated. The axially movable needle 123' is shown with an intermediate side opening 126 and having a closure 127 at its rear end, the closure also serving as a push surface when moving the needle from its rear position to its front position, and the closure is arranged to be affected by a driver structure 150 on the second arm 142. The container 120' is illustrated with a lateral extension 128 at the container front 122' which lateral extension 122' can be penetrated by the needle 123' so that needle opening 126 becomes situated within the lateral extension and in fluid communication with container 120' interior. The container 120' is located in housing 110 about in the same position as in FIG. 1B whereas plunger 161' is situated about in the same position as in FIG. 1A, whereby a distance is present between plunger 161' front end and the movable wall 125, which distance is about equal to the penetration stroke length indicated by arrow 151. Plunger 161' has an additional tooth 162', for bringing it initially up to the movable wall 125, which tooth is initially in contact with pusher 149.

In FIG. 1C the device before penetration is shown in solid lines and after penetration in phantom lines. A first depression of the control button will move the second arm 142 forwards a length corresponding to arrow 151. In this movement driver 150 will affect closure 127 to move needle 123' forwards through container 120' lateral extension 128 to create fluid communication, as described, under simultaneous penetration of needle beyond housing 110 front opening 111'. The needle 123' is then retained in this position by friction or any suitable lock arrangement. In the same movement pusher 149, affecting tooth 162', will bring plunger 161' forwards until it about contacts movable wall 125. As in FIGS. 1A and 1B, release of the control button will move pusher rearwards to override and grip teeth 162 located more to the rear. Repeated depression of the button will move plunger 161' and movable wall 125 successively forwards, causing liquid in container 120' to pass via lateral extension 128 and opening 126 out through the needle 123' for injection. As before, it is presumed that plunger 161' is prevented from moving backwards, e.g. by friction, additional pawl and ratchet mechanisms or any other arrangement.

The schematic device illustrated in FIG. 1 can be modified in various ways, e.g. according to the detailed description above. For example the device may be equipped with a return mechanism, e.g. by inclusion of a return spring and a structure at the rear part of the plunger 161 for release of the lock 180. A dose setting mechanism can be provided on the plunger. Features for initiation of the device can be provided. The link system described can be replaced with another transmission type such as based on wires or wheels. In the embodiment of FIG. 1C the syringe type container can be replaced with any pump arrangement, e.g. a cylinder/piston type for repeated aspiration and ejection strokes through one-way valves, which would make the container choice entirely free, including for example flexible bags.

Figure 1D:
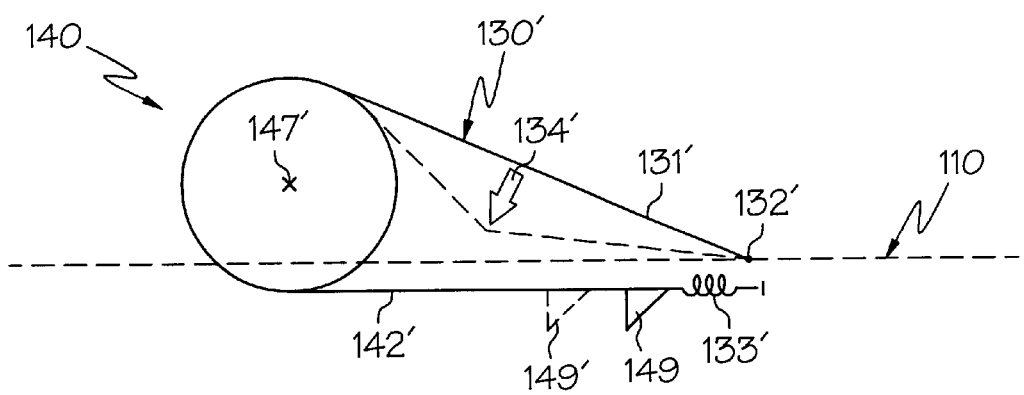
FIG. 1D illustrates schematically a modification of the embodiment of FIGS. 1A and 1B wherein the link arrangement is replaced by a wire or belt arrangement.

In FIG. 1D, a wire or arrangement is shown schematically. As in FIG. 1A, the upper part of the housing 110, the button 130' and the transmission 140' are shown. A wire or belt has one end 132' attached to the housing and continued forward into a manually accessible part 131 ' of the button 130'. The wire or belt continues around a wheel rotating around an axis 147' fixed with respect to the housing 110 and further continues into wire or belt segment 142' to the rear end of which is attached to the pusher 149. The wire or belt is kept stretched by spring 133'. Pushing on the manually accessible part 131' of the wire or belt, as indicated by arrow 134', will move pusher 149 forward, as shown in phantom lines. At removal of the push at arrow 134' the spring 133' will again straighten the wire or belt. The pusher 149 will act as in the embodiment of FIGS. 1A and 1B. Use of wire or belts in transmissions for manually applied force is known as such, e.g., as illustrated by the cited FR 2,717,697.

Figure 1E:
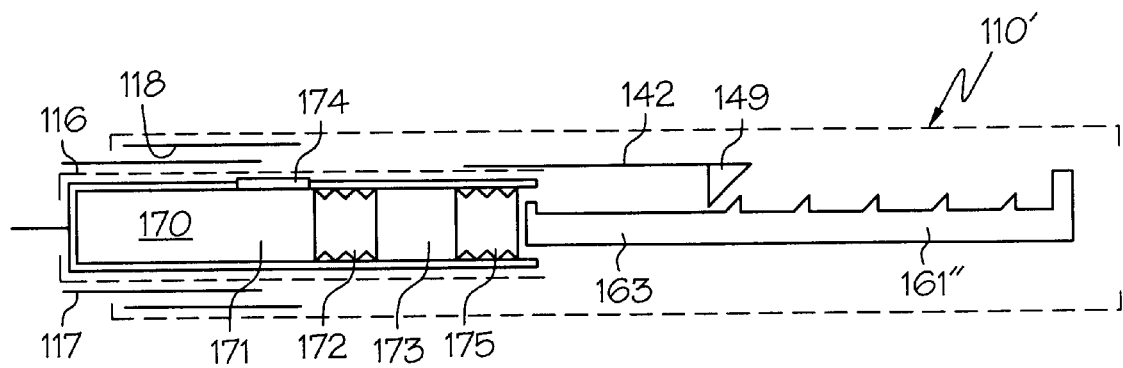
FIGS. 1E and 1F illustrate schematically a modification of the embodiment of FIGS. 1A and 1B wherein the single chamber container is replaced with a dual chamber container.
Figure 1F:
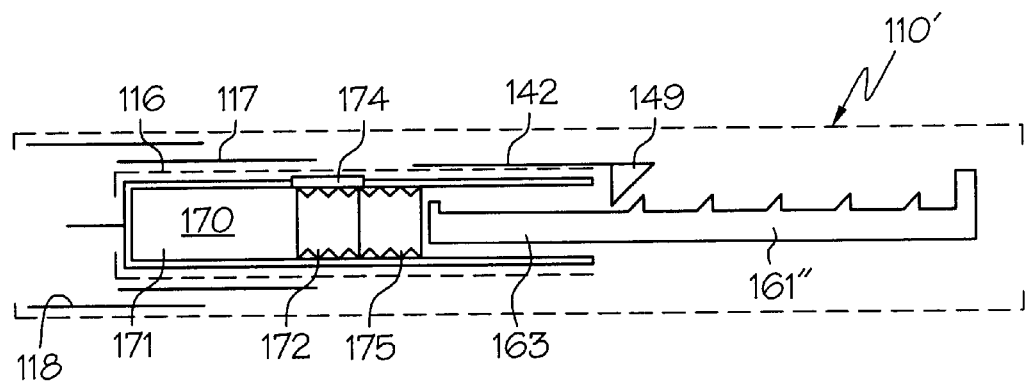

In FIGS. 1E and 1F, a dual chamber container is shown. As in FIG. 1A, the housing 110', the container 170, the second arm 142 and the pusher 149 of the transmission and the plunger 161" are shown. The dual chamber container 170 comprises, besides the rear movable wall 175, a front chamber 171, a front piston 172, a rear chamber 173 and a bypass 174 for overflow of liquid from the rear chamber to the front chamber. In this embodiment the container 170 is enclosed in a sleeve 116 with outer threads 117 designed to cooperate with inner threads 118 on housing 110'. The plunger 161" is also modified with an extended front part 163 for the mixing process to be described. In use, the operator engages the outer threads 117 of sleeve 116 with the inner threads 118 of housing 110' and screws the parts together until front part 163 of plunger 161 " abuts movable wall 175, as depicted in FIG. 1E. Continued movement will first move movable wall 175, rear chamber 173 and front piston 172 forward in concert until the front piston coincides with bypass 174 after which fluid in rear chamber 173 overflows front chamber 171 to reach the situation depicted in FIG. 1F. The dual chamber use manner described is known as such, e.g., from the cited U.S. Pat. No. 4,968,299. From this point on, the device can be operated as described in connection with FIGS. 1A and 1B.

Figure 2A:
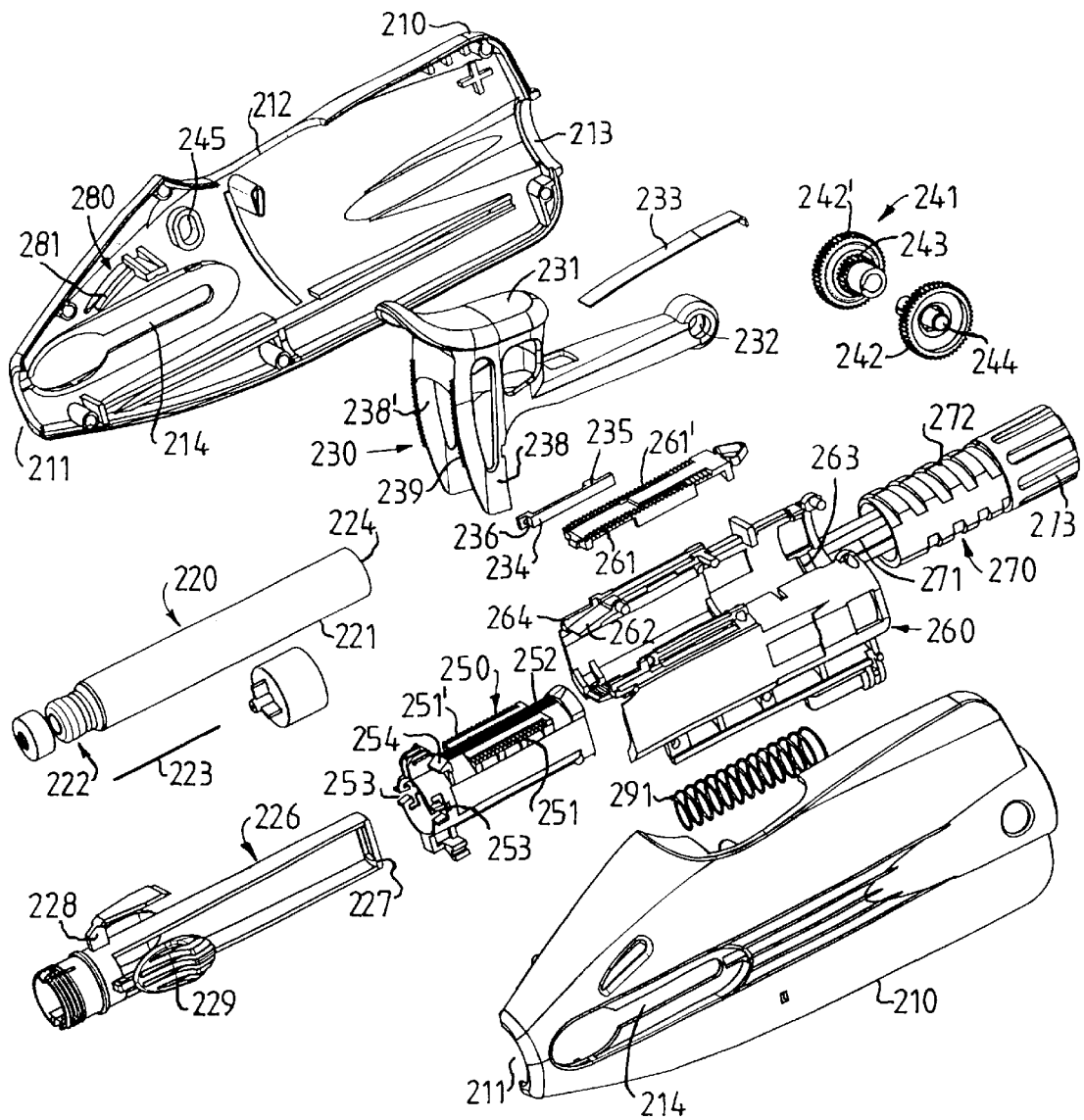
Figure 2B:
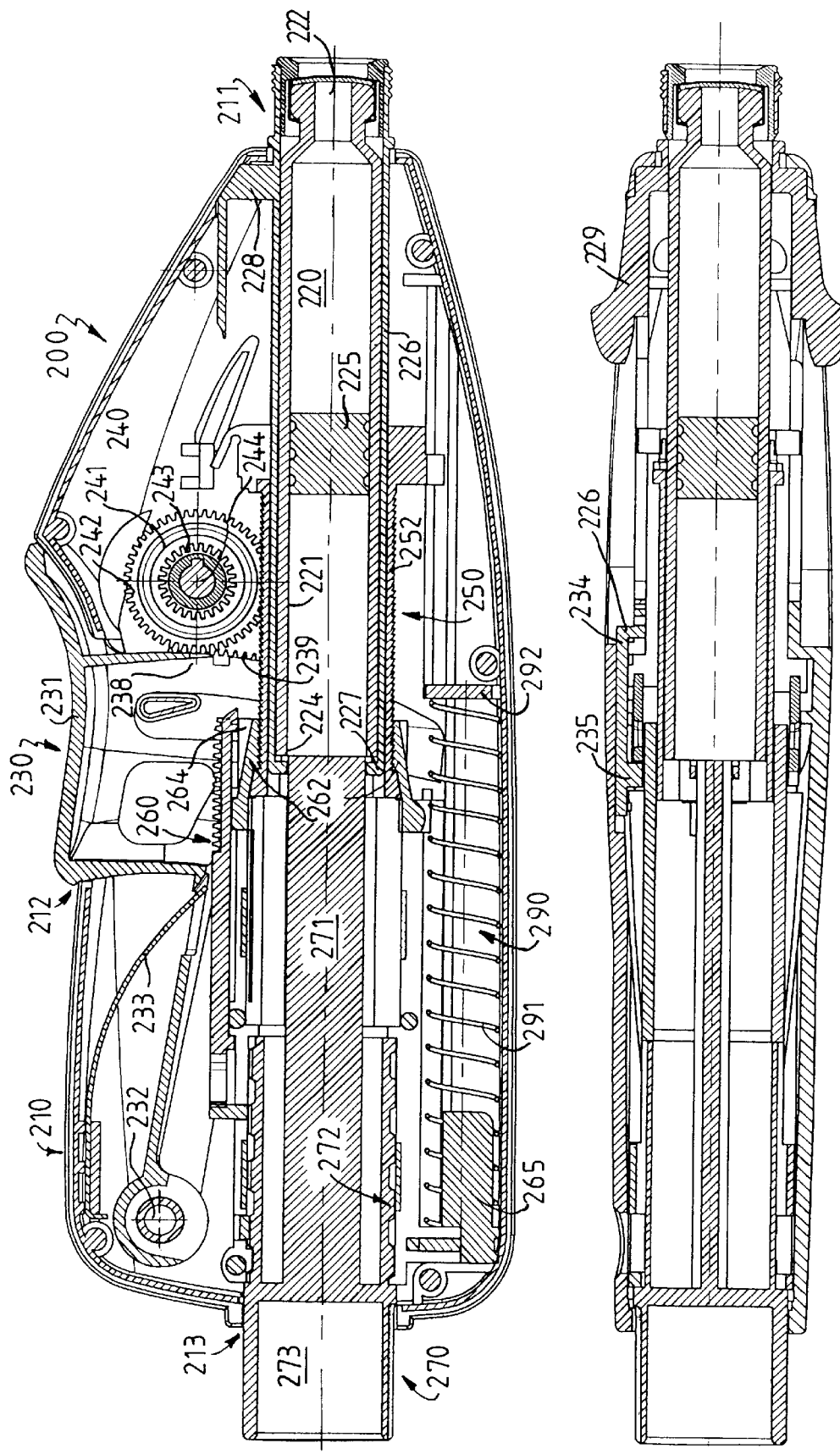

FIGS. 2A to 2G show a detailed embodiment of an injector in several operational phases, including initiation steps, dose setting steps, penetration, injection and needle retraction. The device parts will be described mainly with reference to FIGS. 2A and 2B, showing the device components and the assembled device in an initial state suitable for delivery to a customer. The injector, generally designated 200, comprises a housing 210, made in two halves, with a front opening 211 for needle and container exposure, a side opening 212 for the control button and a rear opening 213 for a dosing screw. A syringe type container 220 is arranged in the housing and comprises a barrel 221, a front 222 with needle 223, a rear barrel end 224 and a movable wall 225 in the form of a piston inserted in the barrel. The container is enclosed in a carrier 226 in partial sleeve and cage form having a rear flange 227 retaining the rear barrel end 224 and at its front adapted to receive a needle attachment and having a radial stop pin 228, with a rearward extension, for limitation of carrier movements. In FIG. 2B the carrier is at its forward extreme, exposing not only the needle but also the container front part outside the housing front opening 211, and stop pin 228 abuts the interior of housing front part. From this position the carrier can be manually moved rearwards by use of externally accessible knobs 229 at both sides of the housing, the knobs being connected to the carrier sleeve part by necks running in slits 214 along the housing sides. A control button, generally designated 230, can be said to include a manually accessible part 231, pivoting around a button axis 232 extending in the width direction of the housing and being biased towards a position most remote from the housing by a button spring 233. In FIG. 2B, however, the button is shown in its depressed state and is retained in this state by a button hook 234, which button hook 234 has a rear hook 235 part for engaging the button and a front end 236 to be affected by the knobs 229 when the carrier is moved rearwards. The button also has two cams 238 and 238', one on each side of the carrier, the front cam surfaces 239 of the cams having a circle segment form, centered around button axis 232, and provided with teeth corresponding to the gear wheel to be described. Instead of being described as apart of the generic button concept the cams can optionally be regarded as part of the generic transmission concept to be described. As in the embodiment of FIG. 1 the force applied to the button has at least a component perpendicular to the container 220 and the button is located lateral to the container axis and at lest partially along the container. A transmission, generally designated 240, can be said to include the toothed gear wheel 241, having two outer large wheels 242 and 242' and an intermediate small wheel 243 of less diameter, providing another gear ratio, arranged mutually fixed on a common wheel axis 244, supported in a bearing 245 fixed to the housing but being enlarged in at least the housing height direction, allowing the gear wheel to move upwards and out of engagement with the toothed rails to be described The large wheels 242 and 242' are always in engagement with the cam surfaces 238 and 238' for clockwise (as shown in FIG. 1A) rotation when the button is depressed and anti-clockwise rotation when the button is released. The transmission parts so far described can be regarded as common for the penetration arrangement and the injection arrangement. Further details of the penetration arrangement can be said to include a penetration sleeve 250, surrounding and driving the container 220 arid its carrier 226 axially between its rear and forward positions, comprising two toothed penetration rails 251 and 251', spaced for cooperation with the large wheels 242 and 242', a ratchet rack 252 with forward tilted teeth for cooperation with a similar structure on the injection sleeve to be described, captures 253 for locking the necks of knobs 229, and catches 254 for cooperation with a lock for the container in the forward position to be described Further details of the injection arrangement can be said to include an injection sleeve 260, surrounding the penetration sleeve and incorporating plunger and dose setting details to be described. The injection sleeve comprises two toothed injection rails 261 and 261', arranged for cooperation with the small wheel 243, an interior pawl 262 with rearward tilted teeth for cooperation with the ratchet rack 252 on the penetration sleeve, securing forward movement only of the injection sleeve with respect to the penetration sleeve, nut teeth 263, for cooperation with a screw in the dose setting unit, a ramp surface 264, for release of the lock to be described, and a spring support 265 for a return spring to be described. The dose setting unit 270 comprises a front plunger part 271, arranged for action on the movable wall 225 during injection, having a threaded intermediate part 272, the treads of which cooperates with the nut teeth 263 of the injection sleeve 260, and a rear dose setting knob 273, manually accessible through the housing rear opening 213. A lock 280 on the housing interior has resilient member 281 being biased towards the container 220 and positioned to flex up and move down behind the catches 254 on the penetration sleeve 250 at the end of the penetration movement, preventing rearward movements during subsequent injection steps. The lock is arranged to be released again at the end of the injection phase when the ramp surface 264 of the injection sleeve 260, always being displaced the same distance independent of the dose set, arrives at the lock 280 and lifts the resilient member 281, enabling a needle return step. A return arrangement 290 can be said to additionally include a return spring 291, acting between the spring support 265 on the penetration sleeve 260 and a foundation 292 fixed to the housing.

Figure 2C:
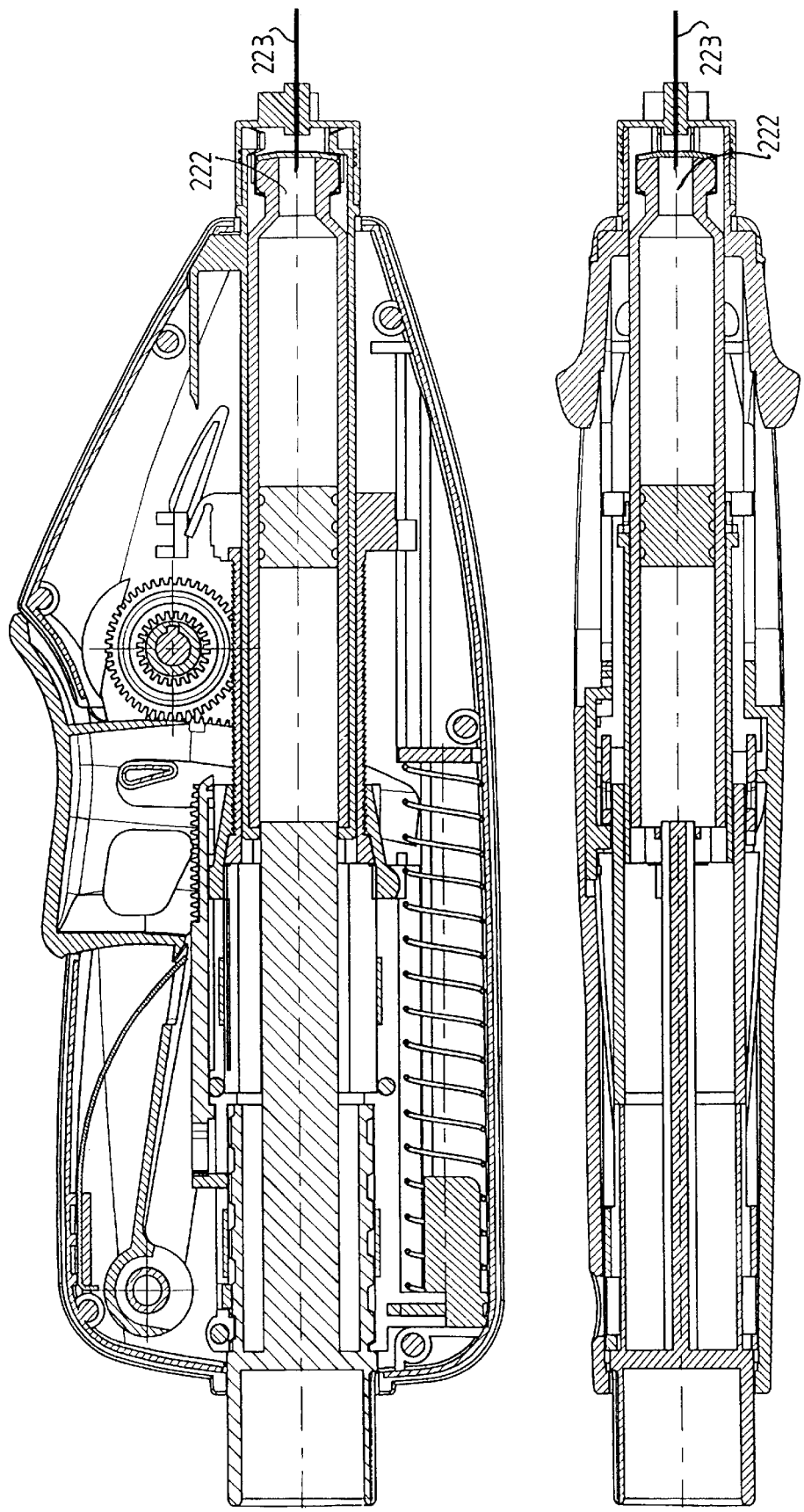
Figure 2D:
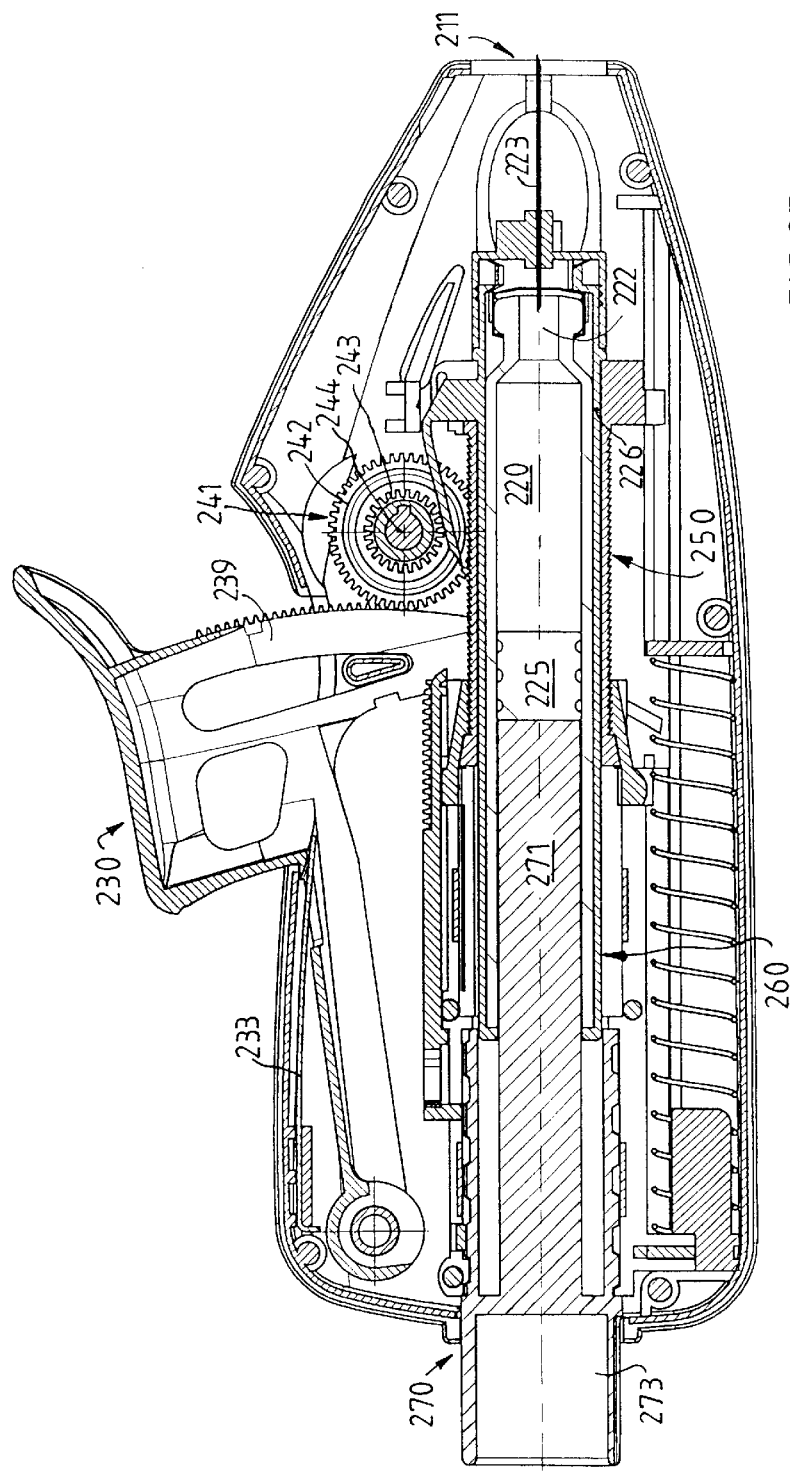
Figure 2D:
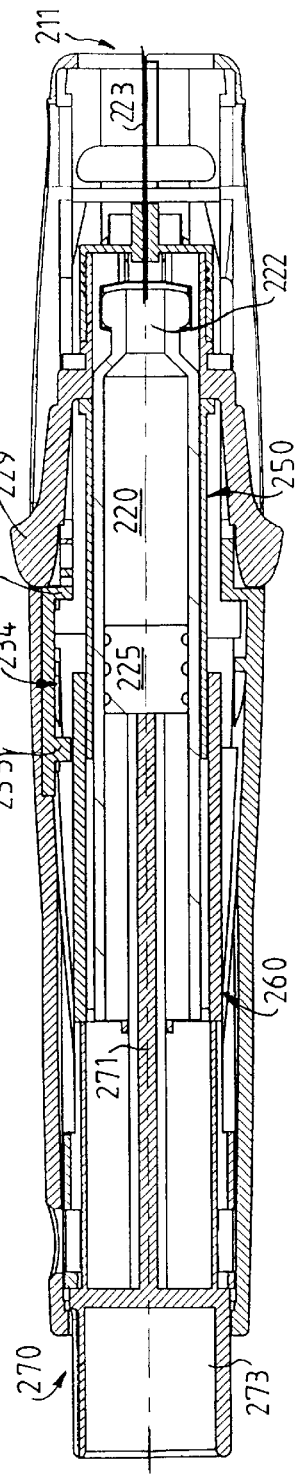

FIG. 2B illustrates an initial state of the device with locked button 230 and the container 220 at a forward extreme. The device can be delivered in this mode, normally without needle attached to the container front. A first user step is then to attach the needle 223 at the exposed container front 222 and remove any needle shield present. FIG. 2C shows the device after these steps. The user then holds the device with the needle upwards and grips and pushes the lateral knobs 229 rearwards until their necks are engaged in the captures 253, as shown in FIG. 2D. The container 220 and its carrier 226 is then locked in relation to the penetration sleeve 250 and the distance traveled is adapted to hide the container front and the needle completely within the housing and behind the rim of housing front opening 211. In the same movement the knobs 229 arrives at button hook 234 front end 236 and move the button hook rearwards to release the rear hook 235 to disengage the button 230 which, under influence of button spring 233, moves to the remote position ready for action. The position of the plunger 271 tip in the dose setting unit 270 is also adapted so that it abuts and displaces the movable wall 225 a certain distance during the last part of the container travel before capture of the knobs 229, which serves to de-aerate the container. If less than the maximum dose is desired the user may now turn the dose setting knob 273 to move the dose setting unit 270 with plunger 271 rearwards, creating a distance between the plunger and the movable wall 225, corresponding to the amount to be left after injection, since the injection sleeve 260 is arranged to make a standard forward movement independent of the dose set. The user may now contact housing front opening 211 to an injection site and press button 230, which will first cause cam surfaces 239 and 239' to secure that gear wheel axis 244 is moved down in bearings 245 and large wheels 242 and 242' into engagement with penetration rails 251 and 251' and then rotate the gear wheel 241 clockwise (FIG. 1A), pushing the penetration sleeve with container 220 forwards until penetration sleeve catch 254 engages the lock 280 resilient arm 281. As best seen in FIG. 2E, this movement exposes the needle 223 in front of the housing front opening to perform site penetration and also moves the dose setting knob 273 to an inaccessible position within the housing. The movement is shorter than the rearward movement of the container performed initially with knobs 229. This in order to limit the exposure to the needle 223 proper and not to expose the front 222 of the container, which was initially made only to facilitate needle attachment. In this movement the interengagement between pawl 262 on the injection sleeve 260 and the ratchet rack 252 on the penetration sleeve 250 secures that the injection sleeve 260, including the dose setting unit 270, is also brought forward. Accordingly the penetration movement takes place against the force of return spring 291 and if the button is released at any time before the penetration sleeve 250 has been caught by lock 280 the return spring 291 will bring the parts back again under withdrawal of the needle, e.g. allowing a new target site selection. After engagement of lock 280 release of button 230 will move it back to its start position in idle run because the rearward force on the gear wheel 241 lifts its axis 244 in bearings 245 from engagement with the penetration rails 251 and 251'. At the locked position the gear wheel 241 small wheel 243 has arrived at a point over the injection rails 261 and 261' and the large wheels are at the end of penetration rails. Next depression of the button 230 will bring the small wheel into full engagement with the injection rails 261 and 261 ' and the clockwise rotation of the gear wheel 241 will move the injection sleeve 260 forwards relative the locked penetration sleeve 250. Accordingly the parts involved at the intersection of the rails will act as a switch system allowing change over from penetration to injection. The less diameter of the small wheel will give a force amplification during the injection phase, requiring a larger button movement for a corresponding sleeve movement. This may require several strokes on the button for full forward displacement of the injection sleeve 250. Again, any release of the button will bring the small wheel 243 out of engagement with the injection rails 261 and 261' and back again during. button depression, while pawl 262 and ratchet rack 252 prevent any rearward movement of the injection sleeve 260. Accordingly the parts involved acts as a reconnect system allowing repeated actions on the button. The operator may use any combination of full or partial button strokes during the injection phase until the injection sleeve has been fully moved forwards to its predetermined end position, as shown in FIG. 2F, at which point the ramp surface 264 lifts lock 280 resilient member 281, enabling the return spring 291 to retract the, now shorter, aggregate of container 220 with needle, penetration sleeve 250, injection sleeve 260 and dose setting unit 270, possibly assisted with a small button release, back into the housing, hiding the needle and with the dose setting knob 273 still unexposed, as shown in FIG. 2G. In this final position the rearward extension of stop pin 228 serves to permanently lift wheel axis 244 to its upper, disengaged, position by preventing small wheel 243 from further engagement with injection rail 261 and 261', hereby also making the button 230 nonfunctional. Since all critical part and operating controls are now disabled or hidden the device can safely be disposed of.

Figure 3:
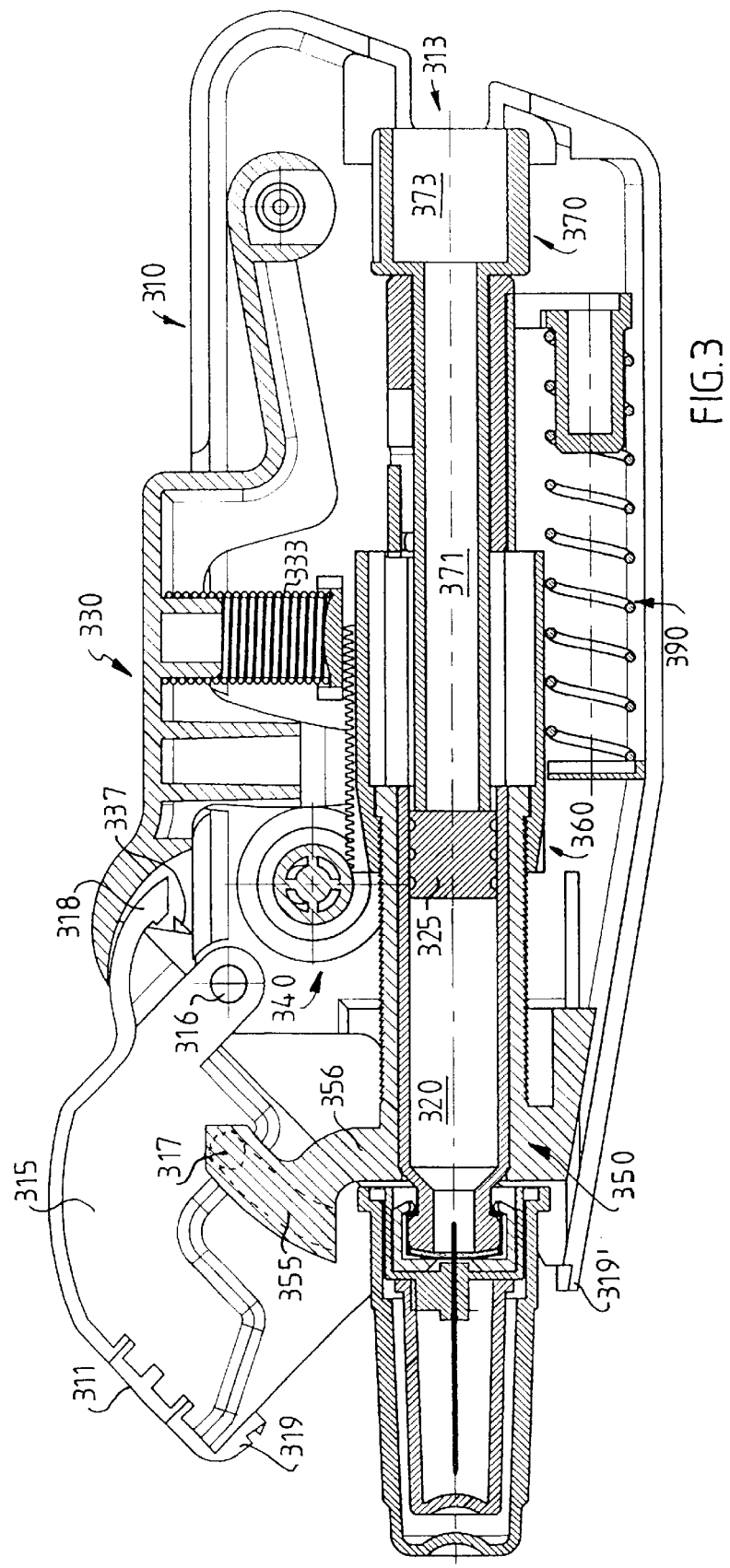
FIG. 3 illustrates a similar to that of FIG. 2 but modified with a lunged door in the front.

In the embodiment of FIG. 3 the housing 310 incorporates a hinged door 315 in the front of the device, which door has a front opening 311 for the needle and is pivotable around axis 316. On the inside of door 315 is a follower pin 317 (dotted lines), arranged to cooperate with a track 355 (dotted lines) on an upper extension 356 of a penetration sleeve 350. The control button 330 here also comprises a temporary lock 337, cooperating with a lock structure 318 on the door. The button spring 333 is here made as a coil spring. Door lock parts 319 and 319' on door and housing respectively are arranged to lock the door permanently when fully closed. As in the embodiment of FIG. 2 the device incorporates a transmission 340, a penetration sleeve 350 with container 320, an injection sleeve 360 and a dose setting unit 370 with dose setting knob 373 at housing rear opening 313 and with a front plunger part 371, arranged for action on the container movable wall 325, a lock (not shown) at the end of penetration and a needle return arrangement 390.

I FIG. 3 the device is shown in an initial state in which it can be delivered to an end user. The user may first remove the needle shields at the front and preferably the door and shields are mutually designed to prevent closure of the door until the shields are removed. It is recommended that the user points the needle upwards before closing the door because de-aeration and pre-ejection takes place simultaneously. When closing the door 315 around axis 316 pin follower 317 cooperates with track 355 to press the penetration sleeve 350 rearwards, which will also bring the injection sleeve 360 and dose setting unit 370 rearwards, hereby withdrawing the needle behind front opening 311 and exposing dose setting knob 373 at housing rear opening 313. During the last part of the rearward movement the injection sleeve 360 with dose setting unit 370 is stopped against a housing structure (not shown) so that the remaining movement is made by the penetration sleeve 350 with container 320 against the stopped parts whereby front plunger part 371 displaces the movable wall 325 forwards relative the still moving container 320, which displacement is adapted for de-aeration and pre-ejection purposes. Also during closing of the door 315 temporary lock 337 of button 330 goes out of engagement with locking structure 318 of the door whereby the button 330, under influence of button spring 333, snaps out to its remote position, ready for action. When the door is fully closed door lock parts 319 and 319' engage permanently and the follower pin 317 leaves track 355 at its lower end to allow free movement of penetration sleeve 350. The device is now ready for use in same manner as described in relation to FIG. 2, i.e. optional dose setting with knob 373, button 330 operation to perform needle penetration, one or several repeated button depressions to perform injection and automatic needle return at injection sleeve arrival at its forward extreme.

The exemplified embodiments are illustrative only and shall not be understood in any way to limit the scope or generality of the invention as defined in the claims.

Generally the exemplified categorizing of the device parts or part groups, and their interfacing, under the various generic concepts used shall not be understood as limiting or compulsive as long as parts are present to meet the intended function or performance of said concepts.

What is claimed is:

1. Injector for containers having an opening with or for an injection needle, the container optionally being of syringe type with a barrel of substantially constant axial cross-section and including a barrel front, the opening for the needle being arranged at the barrel front, and at least one movable wall, optionally with a piston rod connected thereto, inserted in the barrel, the injector for the containers comprising a) a housing, b) a seat or carrier, arranged for reception of the needle or container and for allowing movement of the needle or container, respectively, in relation to the housing, in the axial direction between a rear, needle-covering, position and a forward, needle-exposing, position, c) a penetration arrangement operable to move the needle from the rear position to the forward position, d) optionally a return arrangement operable at least to move the needle in the rearward direction, e) an injection arrangement operable at least to expel container content through the needle, f) at least one control button arranged on the housing and operable to perform operation of the penetration arrangement and/or the injection arrangement, g) a separate or integral transmission, incorporating and connecting the penetration arrangement and the injection arrangement to the at least one control button, and adapted to allow manual energy applied on the at least one control button for movement thereof to be transmitted to the penetration arrangement and the injection arrangement, respectively, for operation thereof under movement of the control button, and h) a switch system adapted to permit phase shift of manual energy applied to the at least one control button first to operate the penetration arrangement and then to operate the injection arrangement.

2. The injector of claim 1, wherein the penetration arrangement is arranged to act directly on the needle, the container or the carrier.

3. The injector of claim 1, wherein the button is arranged for movement with at least a component perpendicular to the needle axis.

4. The injector of claim 3, wherein the button is arranged for guided translational movement.

5. The injector of claim 3, wherein that the button is arranged for at least partial rotational movement around a rotation axis.

6. The injector of claim 5, wherein the rotation axis is oriented substantially along the housing width direction.

7. The injector of claim 3, wherein the transmission comprises a redirect arrangement adapted to redirect the force applied to the button into an axial movement for the needle and/or movable wall.

8. The injector of claim 7, wherein the redirect system is mechanical.

9. The injector of claim 8, wherein the redirect system comprises a wire, a belt, a link system or a lever arrangement.

10. The injector of claim 8, wherein the redirect system includes a wheel.

11. The injector of claim 10, wherein the wheel is a toothed wheel.

12. The injector of claim 1, wherein the button is located lateral to the needle axis.

13. The injector of claim 12, wherein the button is located at least partially between axial ends of the container.

14. The injector of claim 1, wherein the transmission comprises force transforming parts.

15. The injector of claim 14, wherein the force transforming parts provide a higher gear ratio in the injection arrangement compared to a gear ratio in the penetration arrangement.

16. The injector of claim 1, wherein the switch system is adapted to enable phase shift once the needle is in a forward position exposed from the front of the housing.

17. The injector of claim 16, wherein the location is at or close to the needle forward position for the needle.

18. The injector of claim 16, wherein the switch system includes a lock for the needle in said location.

19. The injector of claim 16, further comprising a structure, with substantially fixed location with respect to the housing, arranged to redirect, unlock or enable the force applied to the button for operation of the injection arrangement.

20. The injector of claim 16, wherein at said location the phase shift is enabled within the movement range of the transmission.

21. The injector of claim 20, wherein the switch system includes a pawl and ratchet type mechanism.

22. The injector of claim 16, wherein when force is applied at a constant location in the housing, the penetration movement is adapted to bring an operative part of the injection arrangement into said constant location in the housing.

23. The injector of claim 22, wherein the operative part is a plunger arrangement for a syringe type container.

24. The injector of claim 23, wherein a change in gear ratio is adapted to take place at the phase shift.

25. The injector of claim 22, wherein at least one wheel is adapted to apply the force at the constant location.

26. The injector of claim 1, further comprising a lock arranged to hold, at least temporary, the needle in the forward position.

27. The injector of claim 1, further comprising a reconnect system adapted to allow repeated operation of the button.

28. The injector of claim 27, wherein the reconnect system is adapted to transmit force when the button is moved in one direction and is adapted to idle when the button is moved in the other direction.

29. The injector of claim 27, wherein the reconnect system is adapted to allow reversible phase action.

30. The injector of claim 27, wherein the reconnect system is adapted to allow reversible penetration movement.

31. The injector of claim 27, wherein the reconnect system is adapted to allow pumping action on the button for intermittent operation of the injection arrangement.

32. The injector of claim 31, further comprising a one-way arrangement for the movable wall of a syringe type container, adapted to prevent rearward movement of the movable wall.

33. The injector of claim 27, wherein the reconnect system includes at least one wheel with movable axis for engagement release.

34. The injector of claim 1, wherein the button is biased towards one end position.

35. The injector of claim 34, wherein the button is biased toward a distal position with respect to the housing.

36. The injector of claim 1, further comprising a return arrangement.

37. The injector of claim 36, wherein the needle is adapted to return by use of stored energy.

38. The injector of claim 37, wherein the needle return is adapted to be triggered by action on the button.

39. The injector of claim 37, wherein the needle is adapted to return by a counterspring adapted to be compressed during penetration movement.

40. The injector of claim 37, wherein the needle return is adapted to be triggered automatically at a predetermined point in the injection procedure.

41. The injector of claim 1, wherein the injector comprises a dose setting mechanism.

42. The injector of claim 1, wherein the seat or carrier is arranged to allow movement of a syringe type container rearwards towards the housing under forward displacement of the movable wall relative the container barrel.

43. The injector of claim 42, wherein the displacement of the movable wall is adapted to provide movable wall break-loose, deaeration, pre-ejection or preparation mixing.

44. The injector of claim 43, wherein the lever includes a hinged door.

45. The injector of claim 42, further comprising a lever for movement of the container.

46. The injector of claim 45, wherein the lever is force amplifying.

47. The injector of claim 1, wherein the housing maximum height, to maximum width, ratio is larger than 1.

48. The injector of claim 47, wherein the housing maximum height to maximum width ratio is larger than 1.5.

49. The injector of claim 1, wherein the housing maximum length to maximum height, ratio is less than 4.

50. The injector of claim 1, wherein the container is a dual or multiple chamber type container.

51. The injector of claim 50, wherein the container attachment to the housing comprises a screw thread, the length of which is adapted to the necessary movable wall displacement for unification of chamber contents.

52. The injector of claim 1, wherein the needle is arranged movable in relation to the container.

53. The injector of claim 52, wherein the container is non-movably arranged in the housing.

54. The injector of claim 1, wherein the container is of syringe type with attached needle for common axial movement.

55. The injector of claim 1, wherein the housing maximum length to maximum height ratio is less than 3.

56. Injector for containers having an opening with or for an injection needle, the container optionally being of syringe type with a barrel of substantially constant axial cross-section and including a barrel front, the opening for the needle being arranged at the barrel front and at least one movable wall, optionally with a piston rod connected thereto, inserted in the barrel, the injector for the containers comprising a) a housing, b) a seat or carrier, arranged for reception of the needle or container and for allowing movement thereof, in relation to the housing, in the axial direction between a rear, needle-covering, position and a forward, needle-exposing, position, c) a penetration arrangement operable to move the needle from the rear position to the forward position, d) optionally a return arrangement operable at least to move the needle in the rearward direction, e) an injection arrangement operable at least to expel container content through the needle, f) at least one control button arranged on the housing and operable to at least initiate operation of the penetration arrangement and/or the injection arrangement, wherein the at least one control button is arranged manually accessible on the housing and is arranged so as to allow a rotational or translational movement with respect to the housing, said movement having at least a movement component perpendicular to the needle axis, and g) a separate or integral transmission, incorporating and connecting at least the penetration arrangement to the at least one control button, and adapted to allow manual energy applied on the at least one control button during said movement to be transmitted to the penetration arrangement for operation thereof to move the needle at least partly from the rear, needle-covering, position towards the forward, needle-exposing, position.

57. Injector for containers of syringe type, comprising a barrel of substantially constant axial cross-section, a front opening and at least one movable wall, optionally with a piston rod connected thereto, inserted in the barrel for the displacement of a container content, the injector comprising a) a housing, b) a seat or carrier, arranged for reception of the needle or container and for allowing movement of the needle or container, respectively, in relation to the housing, in the axial direction, c) an injection arrangement operable at least to displace the container movable wall in the forward direction, wherein the seat or carrier is arranged to allow movement of the container rearwards towards the housing under forward displacement of the movable wall relative the container barrel, and d) a hinged lever arranged for directly or indirectly pressing the container rearwards.

58. The injector of claim 57, wherein displacement of the movable wall is adapted to provide movable wall break-loose, deaeration, pre-ejection or preparation mixing.

59. The injector of claim 57, wherein the lever includes a hinged door.

60. The injector of claim 57, wherein the lever is force amplifying.

61. A method for operating an injector for containers having an opening with or for an injection needle, the injector comprising a) a housing, b) a seat or carrier, arranged for reception of the needle or container and for allowing movement of the needle or container, respectively, in relation to the housing, in the axial direction between a rear, needle-covering, position and a forward, needle-exposing, position, c) a pump mechanism operable to expel container content through the needle, and d) at least one control button operable to move the needle in the axial direction and/or to activate the pump mechanism, the method including the steps of i) moving the needle from the rear position to the forward position, ii) ejecting container content through the needle by activation of the pump mechanism, and iii) optionally moving the needle from the forward position to the rear position, wherein manual force is applied to the at least one control button, and further wherein at least part of the force is transmitted to the needle to displace the needle under movement of the at least one control button in a first operation at least partly from the rear, needle-covering, position towards the forward, needle-exposing, position, and subsequent to the first operation, at least part of the force is transmitted to the pump mechanism to eject container content through the needle.

62. The method of claim 61, wherein, in the first operation, the force is transmitted by application of the force directly on the needle, the container or the carrier.

63. The method of claim 61, wherein the at least one control button is moved in a rotational or translational movement with respect to the housing, said movement having at least a movement component perpendicular to the container axis.

64. The method of claim 63, wherein the force applied to the button is translated into an axial force.

65. The method of claim 61, wherein the ratio between the movement applied to the button to the movement of the needle in the first operation is larger than 0.1 and less than 10.

66. The method of claim 61, wherein a single control button movement is used for the first operation and the second operation.

67. The method of claim 61, wherein, in the first operation, the at least one control button is at least partially released and the needle at least partially moved rearwards in a reversible manner.

68. The method of claim 61, wherein force amplification takes place between the first operation and the second operation.

69. The method of claim 61, wherein between the first operation and the second operation the at least one control button is at least partially released and moved in the opposite direction.

70. The method of claim 61, wherein the at least one control button is moved a second time to perform the second operation.

71. The method of claim 61, wherein the at least one control button is moved several times to perform the second operation.

72. The method of claim 61, wherein the needle is permanently or temporarily locked in the forward position between the first operation and the second operation.

73. The method of claim 61, wherein the needle is moved from the forward position to the rear position in a third operation after the second operation.

74. The method of claim 73, wherein the third operation is triggered by operating a control.

75. The method of claim 74, wherein the at least one control button is used for triggering the third operation.

76. The method of claim 75, wherein the step of triggering is performed by release of the at least one control button after the second operation.

77. The method of claim 75, wherein the at least one control button is moved an additional time for triggering.

78. The method of claim 73, wherein the third operation is performed at a predetermined content of the container.

79. The method of claim 78, wherein the step of performing the third operation is by release of stored energy.

80. The method of claim 61, further comprising a step of setting a dose to be ejected.

81. The method of claim 61, further comprising a step of activating the pump mechanism by movement of a door on the device.

82. A method for operating an injector for containers having an opening with or for an injection needle, the injector comprising a) a housing, b) a seat or carrier, arranged for reception of the needle or container and for allowing movement of the needle or container, respectively, in relation to the housing, in the axial direction between a rear, needle-covering, position and a forward, needle-exposing, position, c) a pump mechanism operable to expel container content through the needle, and d) at least one manually accessible control button operable to move the needle in the axial direction and/or to activate the pump mechanism, the method including the steps of i) moving the needle from the rear position to the forward position, ii) ejecting container content through the needle by activation of the pump mechanism, and iii) optionally moving the needle from the forward position to the rear position, wherein manual force is applied to move the at least one manually accessible control button in a rotational or translational movement with respect to the housing, said movement having at least a movement component perpendicular to the container axis, and at least part of the force is transmitted to the needle to displace the needle in a first operation at least partly from the rear, needle-covering, position towards the forward, needle-exposing, position.

83. A method for operating an injector for containers of syringe type, comprising a barrel of substantially constant axial cross-section, a front opening and at least one movable wall, optionally with a piston rod connected thereto, inserted in the barrel for the displacement of a container content, the injector comprising a) a housing, b) a seat or carrier, arranged for reception of the needle or container and for allowing movement of the needle or container, respectively, in relation to the housing, in the axial direction, c) an injection arrangement operable at least to displace the container movable wall in the forward direction, and d) a hinged member attached to the housing, the method comprising moving the hinged member, and transmitting the hinged member movement into a pressing movement for the container rearwards towards the housing under forward displacement of the movable wall relative to the container barrel.

84. The method of claim 83, further comprising a step of performing movable wall break-loose, deaeration, pre-ejection and/or preparation mixing by displacement of the movable wall.

85. The method of claim 83, wherein the hinged member is a closeable door, the closure of which acts as the hinged member movement.

86. The method of claim 85, wherein at least a part of the container is enclosed by closure of the door.

87. The method of claim 83, wherein a control button is enabled for operation by the movement of the hinged member.

88. The method of claim 83, further comprising a step of amplifying the force applied to the hinged member when applied to the movable wall.

89. Injector for containers of syringe type, comprising a barrel of substantially constant axial cross-section, a front opening and at least one movable wall, optionally with a piston rod connected thereto, inserted in the barrel for the displacement of a container content, the injector comprising a) a housing, b) a seat or carrier, arranged for reception of the needle or container, c) an injection arrangement operable at least to displace the container movable wall in the forward direction, wherein the injection arrangement comprises at least one rail, at least partly coaxial or parallel with the barrel axis and constituting or being connected to a piston rod or plunger arrangement for displacement of the movable wall at least in the forward direction, and d) a driving wheel with a rotation axis, the axis being connected directly or indirectly to the housing, movably between two axis positions, the wheel in a first position being in engagement with the rail for movement thereof relative the housing and in a second position being out of engagement with the rail.

90. The injector of claim 89, wherein the rail and the wheel are correspondingly teethed.

91. The injector of claim 89, wherein an actuator is connected to the housing in a movable manner and is connected to the driving wheel, optionally via intermediate parts or wheels, for rotation thereof at actuator movement.

92. The injector of claim 91, wherein the actuator is arranged to allow movement under urging of the driving wheel toward the first position.

93. The injector of claim 92, wherein the actuator is connected to the driving wheel for movement of the rail in the forward direction when urging the driving wheel toward the first position.

94. The injector of claim 91, comprising a change of gear ratio between the actuator and rail.

95. The injector of claim 91, wherein the actuator is or includes a second wheel.

96. The injector of claim 91, wherein the actuator is a control button.

97. The injector of claim 96, wherein a connection between the control button and driving wheel includes a cam surface.

98. The injector of claim 97, wherein the control button is rotatable around a button axis on the housing, the cam surface has curvature, and the curvature is centered substantially at the button axis.

\* \* \* \* \*

UNITED STATES PATENT AND TRADEMARK OFFICE
CERTIFICATE OF CORRECTION

PATENT NO.    : 6,599,272 B1
DATED         : July 29, 2003
INVENTOR(S)   : Birger Hjertman et al.

It is certified that error appears in the above-identified patent and that said Letters Patent is hereby corrected as shown below:

Column 23,
Line 35, delete "that".

Column 25,
Line 11, change "height, to maximum width, ratio" to -- height to maximum width ratio --.
Line 15, change "height, ratio" to -- height ratio --.

Signed and Sealed this

Ninth Day of December, 2003

JAMES E. ROGAN
*Director of the United States Patent and Trademark Office*